(12) United States Patent
Kulkarni et al.

(10) Patent No.: US 9,763,998 B2
(45) Date of Patent: Sep. 19, 2017

(54) SERPINS: METHODS OF THERAPEUTIC β-CELL REGENERATION AND FUNCTION

(71) Applicant: Joslin Diabetes Center, Inc., Boston, MA (US)

(72) Inventors: Rohit N. Kulkarni, Chestnut Hill, MA (US); Abdelfattah El Ouaamari, Boston, MA (US); Daniel Margerie, Frankfurt am Main (DE); Matthias Lohmann, Frankfurt am Main (DE); Jean Claude Guillemot, Espanes (FR); Denis Loyaux, Belbeze (FR)

(73) Assignee: Joslin Diabetes Center, Inc., Boston, MA (US)

( * ) Notice: Subject to any disclaimer, the term of this patent is extended or adjusted under 35 U.S.C. 154(b) by 0 days.

(21) Appl. No.: 14/186,054

(22) Filed: Feb. 21, 2014

(65) Prior Publication Data

US 2015/0366940 A1 Dec. 24, 2015

Related U.S. Application Data

(60) Provisional application No. 61/767,948, filed on Feb. 22, 2013.

(30) Foreign Application Priority Data

Feb. 22, 2013 (EP) ..................... 13305204

(51) Int. Cl.
*C07K 14/81* (2006.01)
*A61K 38/17* (2006.01)
*A61K 38/55* (2006.01)

(52) U.S. Cl.
CPC .......... *A61K 38/1709* (2013.01); *A61K 38/55* (2013.01)

(58) Field of Classification Search
CPC ............................ A61K 38/1709; A61K 38/55
See application file for complete search history.

(56) References Cited

U.S. PATENT DOCUMENTS

| | | | |
|---|---|---|---|
| 5,370,991 A | 12/1994 | Remold-O'Donnell | |
| 5,663,299 A | 9/1997 | Remold-O'Donnell | |
| 5,827,672 A | 10/1998 | Remold-O'Donnell | |
| 2007/0072798 A1* | 3/2007 | Salonen ............. | A61K 38/1709 514/4.9 |
| 2010/0184658 A1 | 7/2010 | Gelber | |

FOREIGN PATENT DOCUMENTS

| | | |
|---|---|---|
| WO | 2006037606 A2 | 4/2006 |
| WO | 2007006858 A2 | 1/2007 |

OTHER PUBLICATIONS

Silverman et al., The Serpins are an Expanding Superfamily of Structurally Similar but Functionally Diverse Proteins, JBC, published Jul. 2, 2001 as Manuscript R100016200.*
Khan et al., Journal of Amino Acids, vol. 2011, Article ID 606797, 10 pages.*
Gurda et al., Physiol Genomics. Jan. 2012; 44(1): 14-24.*
Kalis et al., Islets, 2.3 185-189, May/Jun. 2010.*
Ryan et al., Successful Islet Transplantation Continued Insulin Reserve Provides Long-Term Glycemic Control, Diabetes, vol. 51, Jul. 2002, pp. 2148-2157.*
Estall & Drucker, Tales beyond the Crypt: Glucagon-Like Peptide-2 and Cytoprotection in the Intestinal Mucosa, Endocrinology, Jan. 2005, 146(1):19-21.*
De Leon, Identification of transcriptional targets during pancreatic growth after partial pancreatectomy and exendin-4 treatment, Physiol. Genomics 24:133-153 (2006).*
Benarafa, Charaf et al., "SerpinB1 protects the mature neutrophil reserve in the bone marrow", Journal of Leukocyte Biology, vol. 90: 21-29, Jul. 2011.
Blüher, Matthias, "Vaspin in obesity and diabetes: pathophysiological and clinical significance", Endocrine, vol. 41(2):176-82, Apr. 2012.
Choi, Sung Hee et al., "Clinical implications of adipocytokines and newly emerging metabolic factors with relation to insulin resistance and cardiovascular health", Frontiers in Endocrinology, vol. 4(97): 1-7, Aug. 2013.
El Ouaamari, Abdelfattah et al., "Liver-Derived Systemic Factors Drive b Cell Hyperplasia in Insulin-Resistant States", Cell Reports, vol. 3: 401-410, Feb. 21, 2013.
Extended European Search Report for European Application No. 13305204.3 dated Aug. 9, 2013.
Extended European Search Report for European Application No. 13306284.4 dated Feb. 7, 2014.
Gong, D. et al, "Critical Role of SerpinB1 in Regulating Inflammatory Responses in Pulmonary Influenza Infection", Journal of Infectious Diseases, vol. 204(4): 592-600, Aug. 15, 2015.
International Search Report for PCT/EP2014/053419 dated Apr. 11, 2014.
International Written Opinion for PCT/EP2014/053419 dated Apr. 11, 2014.
Shaker, Olfat G. et al. "Vaspin gene in rat adipose tissue: relation to obesity-induced insulin resistance", Molecular and Cellular Biochemistry vol. 373(1): 229-239, Jan. 2013.
Huntington, J. A. "Serpin structure, function and dysfunction." Journal of Thrombosis and Haemostasis 9(Suppl. 1): 26-34, 2011.
De Leon, Diva D. et al. "Identification of transcriptional targets during pancreatic growth after partial pancreatectomy and exendin-4 treatment." Physiological Genomics, vol. 24: 133-143, 2006.
Menge, Bjoem A. et al. "Partial Pancreatectomy in Adult Humans Does Not Provoke Beta-Cell Regeneration." Diabetes, vol. 57: 142-149, Jan. 2008.
Wang, Li et al. "Identification of SERBINB1 As a Physiological Inhibitor of Human Granzyme H." The Journal of Immunology, vol. 190: 1319-1330, Dec. 26, 2012.

* cited by examiner

Primary Examiner — Karlheinz R Skowronek
Assistant Examiner — Joseph Fischer
(74) Attorney, Agent, or Firm — McNeill Baur PLLC

(57) ABSTRACT

Compositions and methods of use are provided for improving β cell function and promoting pancreatic β cell proliferation in vitro, in vivo and ex vivo. The active agents of the pending invention comprise Serpin family peptides (e.g., SerpinB1), functional and structural analogs of Serpin family peptides and nucleic acids encoding Serpin family peptides, as well as active fragments thereof.

7 Claims, 25 Drawing Sheets

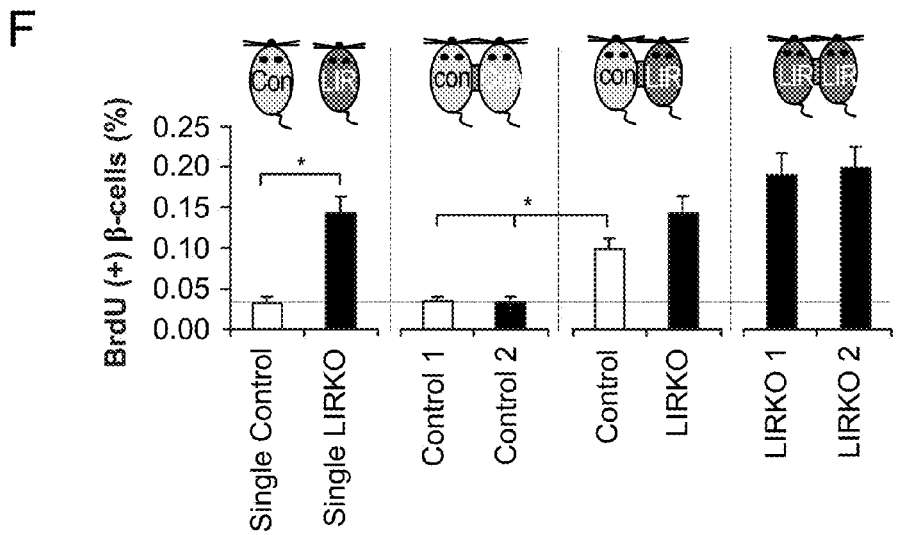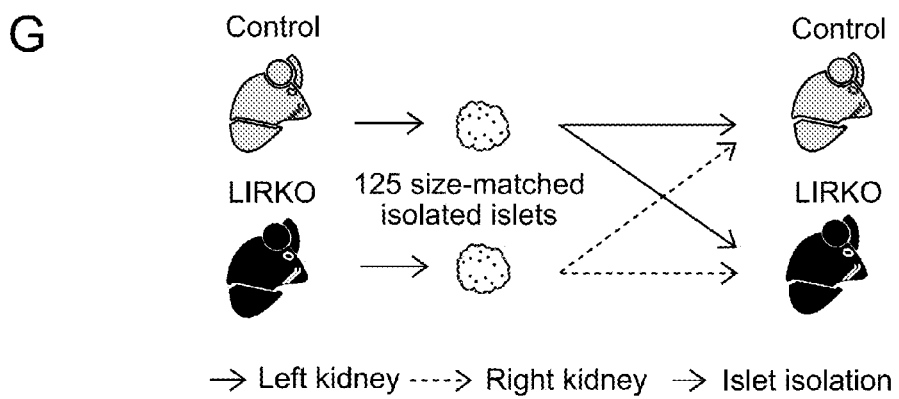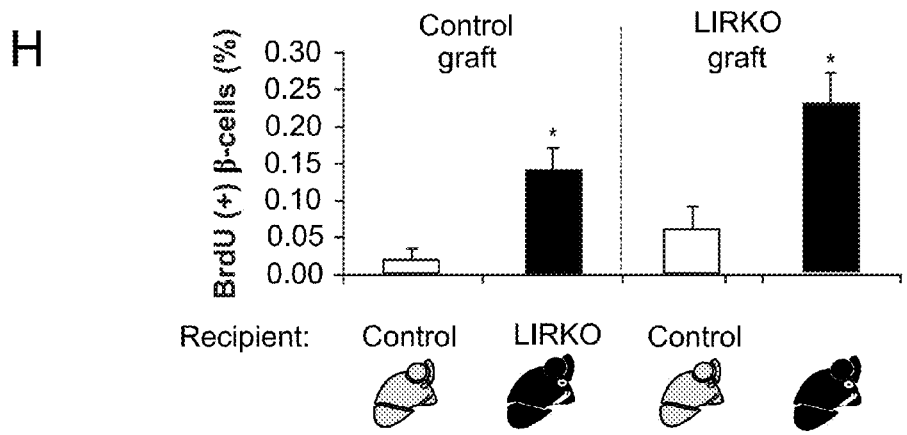
FIG. 2 (cont.)

A
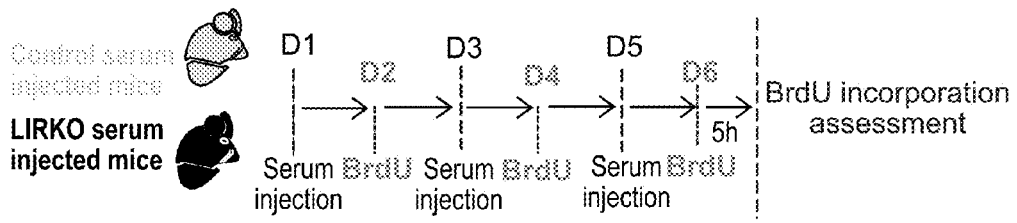
B
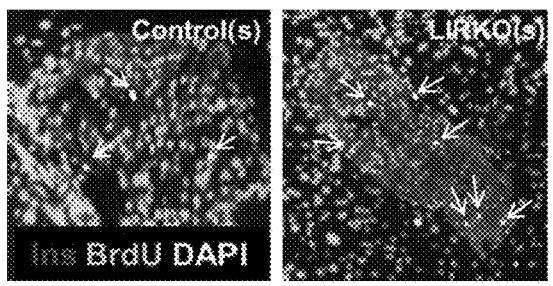
C
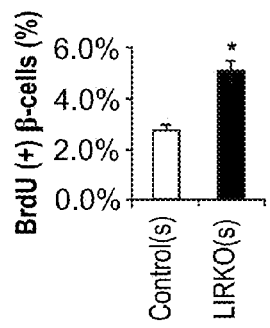
D
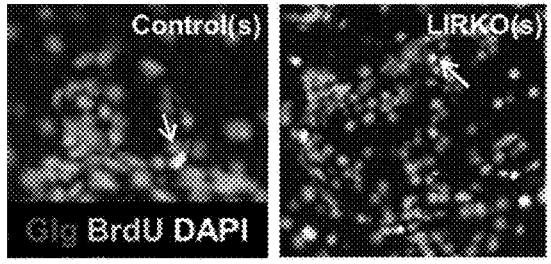
E
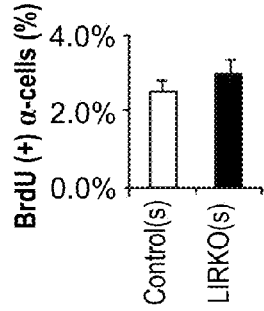
F
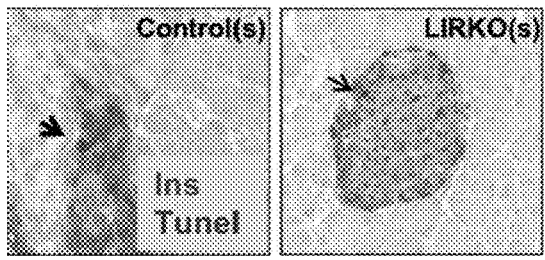
G
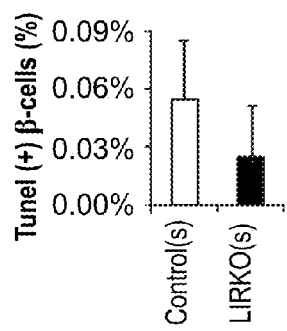
FIG. 3 pancreas: a, e. liver: b, f. visceral adipose: c, g. subcutaneous adipose: d, h. skeletal muscle: i, m. kidney: j, n. lung: k, o. spleen: l, p.

↑ lipid droplets
↑ lymphocyte infiltration

Mouse:
>gi|114158674|ref|NM_025429.2| Mus musculus serine (or cysteine) peptidase inhibitor, clade B, member 1a (Serpinb1a), mRNA (SEQ ID NO: 1).

```
ACTTCATCCTAGCTGTAAGTGGAGCCAGACCTGCTAAGCAAGAGACTTCACCATGGAGCAGCAGCTGAGTTCA
GCCAACACCCTCTTCGCCTTGAGCTGTTCCAAACCCTGAAATGTTCTCACAGGAAAGCAGCCCACAGGAAACATCTTCT
TCTCTCCCTTCAGCATTTTCTTCTGCCTTGACTCTGTTGAGGACATCTAACAGAGCTCACGCTTCCAAAGCCTGCAGCTCA
GCTTTCTAAGACTTTCATTTGACTCTGTTGAGGACATTGCTAAACAGAGCTGCTGAAAGCCTGAATGCTGAA
GTGAGCAAAACGTGGAGCATCTGGCTTCAACACACTGTATGGTGCTGAAACTTGGTGTGCTGACTTGGCCCCTGGATTTTCTGCA
TCCTTCCTGAATACTTGGCTTCAACACGGAGAATAAACCAGTGGGTCAAACTTGTGCTGGTGAAACAGAGCCATCTACTTTAAGGAA
TGCCCTCTGAGGATGCAAGGAGATGATGGTGGTGGCAAATTCATGACCAACAGTATCAGGTCAAACTTGTGCTGGTGAAACAGAGCCATCTACTTTAAGGAA
CTGTGTGTCTGTGGGAGAAATGATGTATCCAGGGTGGACAGTAGAGGACAAAAGAAAAAAACTTAGCAGTGCCTTAAGAAGTGCAAGGTG
AACAGTGAAGATGCCTTAAGAATGTATCCAGGGTGGAAAAGCAAATTGCCACGTCAAATGCTCTTGAATGCTCCAAACGTGAGAA
CCACGGGTCTCTTAAGAAGATTGAAAAGCACGTCAAATGCTGCTTGAATGCTCTTGAATGCTCCAAACGTGAGAGT
CTTGGAATTCATTGATGTCCACGTCAAGATCTCTTTAGCAGTCCTTGTGTTGCCTGAAGTGAGGAGCTGATCTCTCTGGCATGTCAGGAT
AACCTGGGCCGCTGGCAGAGTCTCTTTAGCAGTCCTTGTGTTGCCTGAAGTGAGGAGCTGATCTCTCTGGCATGTCAGGAT
CCAGAGATCTTTTCATATCAAAATTGTCACAAGTCCTTTGTGTTGCCTGGAAGTGAATGAGGAAGAATTCACAGTGGACCAT
AGCCGGTTCATTTTCTTCATTGACAGAGACTTTTACAGATATAAAACTTCTAACCAAGGCAGAGTATGTCTATTTTGATTGTAAACATAGCAGGACTCCTG
CCGTTCATTTTCTTCATTGACAGAGACTTTGCATGACTTTGCATGACCTCAAACTTTGCATGAAAATTCAAAGGGTTCATAGCTAGGCTGAAAATTCTGGA
AGAAGGAGACTTTACAGATAAAACTTTGCATGACCTTTGCATGAGTTCTATTTTGATTGTAAACATAGCAGGACTCCTG
TTTTCATTTGTACTTGATCCATGACTTTTGCATGACCTTTGGGTATGTCTATTTTGATTGTAAACATAGCAGGACTCCTG
AGCTCTTTATATCCGGCTTCAAACTTTGCATGACCTTCAAATCTGCTTTTCAAGTACAACAGTCTGTGAAGAT
TTTTCATTTGTACTTGATCCATGACTTTTGCATGACCTTTGGGGTTATGCTAACTGAAGTCATATCAACATCCAGAGT
CGACTCCATCCTGTTTATGCAGCCCTCAAATGCTGCTGGGCAGCCCTCAAATGCTGCTGTACTTTAGCAGGTCAGATACTTTAGCAGGCTGAAGTCATATCAACATCCAGAGT
GGGTAGCGTGAAGATAAACAGTGCTGCTTTTGGGTTATGCAGCCCATGCTGCCTGTACTTTAGCAGGTCAGATACTTTAGCAGGCTGAAGTCATATCAACATCCAGAGT
ATAATCAAAGACAGTGAACCATGAAAGATCCAAGGCTCTAAATGCTGCAGGCTGGTACTTTAGCAGGTCAGATACTTTTAAAACATTCATGCT
AGGACACAGTGAACCATGAAAGATCCAAGGCTCTAAATGCTGCAGGCTGGTACTTTAGCAGGTCAGATACTTTTAAAACATTCATGCT
AATATTGACGAAATCCAAGGAACTAGAAACCCCAGAGCTTAAACATATAAATTATTTTCCATTGAAAACTTAAATAA
GGATGAAAAGGAACTAGAAACCCCAGAGCTTTGAATGCTGTTAAACATATAAATTATTTTCCATTGAAAACTTAAATAA
TAAAGAATTTGTGGATTTTTAAGTCTGAAAAAAAAAAA
```

FIG. 13

Human:
>gi|401709928|ref|NM_030666.3| Homo sapiens serpin peptidase
inhibitor, clade B (ovalbumin), member 1 (SERPINB1), transcript
variant 1, mRNA (SEQ ID NO: 2).
AGAAAGAAGCCGCGCCCCTGAGGAGGCGCTGCCCGGAAGCCACGCTCACTTCTGCTTGCACTTAGGCGA
CCTCGGGAGCTCGGACCTGCTGCTATAAGAGCCAGTCAGCAGCGGCCCCTCCTTCCTCCGCCCGCCGGG
TGACGCTTCCCGCGTGCCTTCGGCGGCCTGTCCGGTTTTCACCATGGAGCAGCTGAGCTCAGCAAACAC
CCCGGAGCGTGCCCTGTTCCTGGCGCGTTGAGTGAGAACAATCCGGCTGAGAGTAACACGGCAGCACAG
CCTTGGACCTGCTACTGGCCATGGTTTTCTGGGGACCAGAGATTCCAAGAGTCTGAATGCTGATATCTG
TTCATCTGCTCAACACGGTTGAAGAGTTCATTCAAGAGTTCATTATAGAGAGAAAACTTACAATTTCCT
CATTTCAACAAGAATTTCTGACTCAGAAAACAATGGTGCTGACCTGGCCAGTGTGTGGATTTTCAGCAT
CGTCTTATATTCGACTCAGAAAACATAAACCAGTGGTCAAAGGACACAGAAGATAAATGCCATCTATTT
GGTTTCGACTCAGAAAACATAAACCAGTGGTCAAAGGACACAGAAGATAAATGCCATCTATTTCAAGGG
AGGAAGACCATAACATGACCACGAAGCCAAACTTGTGCTAGTAATGCCACCATTCAGATTGAATAAGAC
TGGTTGATAACATGAAGCCACGAATGCACATTGCATATGCCATGGTCATCCTGCTCCTGCCGATGACAT
CATGAAAGAAGAAGCAGCTCAGCATGCTCAATTTCAGATTGAATCGAGGACCCTTAAGTGCCGTGTGCT
TATCAGAAGAAGAAATTTGCATATGCCATGGTCATCCTGCTCCTGCCGATGAGTGGACTAAACCTGAGG
AAGGCGAGGAGCTCAGCATGCTCAATTTGGAAAAAGTTGACTTTGACTAAACCTGAGAATCTCGATTTC
GATTGAGGAACAGTTGCCCAGGTTGCCCAGGTTCAAACTGTTACACTCTCAACTCTCAACCTCCGACCT
GTTAATGTCAGCTTGCCCAGGTTCAAACTGTTACACTCTCAACTCTCAACCTCCGACCTCGCCCCGCCTAG

FIG. 14

```
GTGTGCAGGATCTCTTTAACAGTAGCAAGGCTGATCTGTCTCTGGCATGTCAGGAGCCAGAGATATTTTTAT
ATCAAAAATTGTCCACAACTTTCTGCATGTTGTGGAAGTCATTTGTGGAATGAAGAACAGAGCTGCCACAGCA
GGCATCGCAACTTTCTGCATGTTCTGATGCCCGAAGAAAATTTCACTGCCGACCATTCCATTCCTTTCTTTA
TTCGGCATAATTCCTCAGGTAGCATCCTATTCTTGGGAGATTTTCTTCCCCTTAGAAGAAAGAGACTGT
AGCAATACAAAAATCAAGCTTAGTGTGCTTTATTACCTGAGTTTTTCATTTTGTAAGTTTGGCTCTGTTTA
TACCAATATAAAAACCACTGTTCAGAAAACAAGTCTATTTTCATTTTGTAAGTTTGAAAAAATCCAGTGGTTGCTTTTG
CACCCATGAATTTTGGCATGGGTATCTATTTTCAGAGAAGAATACATCCGATGCGTAGAGATGGTCATTTATTTTGCAGTTAGAATT
AATGCATCAAGTAAAGAATCCTCGATAGCCATGGAAAACATGATAAGGGAGTTGAAGGGACAAGCTTGCCTCGCCTGACTTTTCTGTCCC
AAATTGCTATATCCCTGATAGACAGACACCCTGTTACGAGAGCCAGGTTACAGACCTCTAGTTTAGACTCTTCAATTAAAGGGCCAATGGT
TGTAAGAGAGCACCCCAATTGAGAGCCCAGGTTACGAGACCTCTAGTTTATGTATAATATAGTTCATGTGGCGCTGTAAGATAAACTGC
TTGTTCTGCAGGATTAGTATTCTGTTACAAGATCTACAAAAATAACCAAGAGTCTACAAAAATAACCATGTTTCTTCTCTTTCTTTCTTTCT
TATAACCTGCATTCCCTTTGTTTCTTTCTCTCAGGCTGGAGTGCAGTGGCACGATCTCAG
AAGAAGTGGGTGTCTTTTTTTTTTTTTTTTTGAGACAGAGTCTTGCTCTGTTCAGGCTGGAGTGCAGTGGCACGATCTCAG
TGAACAAAGTTTTTTTTTTTCACCTCACCTCACCGCCTGCCTCCCAGGCTGGAGTGCAGTGGCACGATCTCAG
TTCTTTTTTTTTTTGAGACAGAGTCTTGCTCTGTTACCCAGGCTGGAGTGCAGTGGCACGATCTCAG
CTCACCGCATGCACCACCACATGCACCCCCTCTGCAACCCTGGGTTCAAGTGATTCTCCTGCCTCAGCCTCCCAAAGTGCTGGGATTAT
AGGCATGCACCACCACATGCACCCCCCAAAGTGCTGGGATTACAGGCA
GCTGGTCCCGGAACTCCTGACCTCAAGTGATCCGGCACCTCAGCCTCCCAAAGTGCTGGGATTACAGGCA
TGAGCTACCATGCCCTGGCCCTTTCTGACTCTTGACCTCAAGTGATCCGCGCACCTCAGCCTCCCAAAGTGCTGGGATTACAGGCA
GATGGGTGGGGCTCTTGCTCCCACAGGATGGGCATGATTAATAAAACGTCCTAGGATTCTGCAAGC
CCGCATATTCTTGCTCCCACAGGATGGGCATCATGAATCATGAATTAATAAAACGTCCTAGGATTCTGCAAGC
TAAAAAAAAAAAAAAAAA
```

FIG. 14 (cont.)

SDS/PAGE analysis of secreted proteins from LIRKO and control mouse hepatocytes

A

```
MEQLSSANTL  FALELEFQTLN  ESSPTGNIFF  SPFSISSALA  MVILGAKGST
AAQLSKTFHF  DSVEDIHSRF  QSLNAEVSKR  GASHTLKLAN  RLYGEKTYNF
LPEYLASTQK  FLHASEDARK  EINQWVKGQT  EGKIPELLSV
GVVDSMTKLV  LVNAIYFKGM  WEEKFMTEDT  LSKK        DTKTVKMMYQ
KKKFPFGYIS  DLKCKVLEMP  YQGGELSMVI  LLPKDIEDES  TGLKKIEKQI
TLEKLLEWTK  KADLSGMSGS  RENLEFIDVH  VKLPRFKIEE  SYTLNSNLGR  LGVQDLFSSS
EFTVDHPFIF  FIRHNPTSNV  LFLGRVCSP   KSFVEVNEEG  TEAAAATGGI  ATFCMLLPEE
```

Murine Serpinβ peptide: SEQ ID NO: 3

B

| HUGO-ID | Description | Ratio LIRKO/Control Experiment 1 | p value exp. 1 | Ratio LIRKO/Control Experiment 2 | p value exp. 2 | Ratio LIRKO/Control Experiment 3 | p value exp. 3 |
|---|---|---|---|---|---|---|---|
| SERPINB1 | serpin peptidase inhibitor, clade B, member 1 | 17,5 | 1,50E-03 | 11,6 | 3,80E-15 | 18,0 | 3,70E-14 |

FIG. 16

SERPINS: METHODS OF THERAPEUTIC β-CELL REGENERATION AND FUNCTION

This invention was made with Government support under grant number RO1 DK 607536 awarded by the National Institutes of Health. The Government has certain rights in this invention.

SEQUENCE LISTING

The instant application contains a Sequence Listing which has been submitted electronically in ASCII format and is hereby incorporated by reference in its entirety. Said ASCII copy, created on Dec. 2, 2014, is named JDP-162US03_SL.txt and is 10,204 bytes in size.

BACKGROUND OF THE INVENTION

Diabetes has reached epidemic proportions in both developed and developing countries, and the cost of treating individuals with complications resulting from uncontrolled hyperglycemia is a major economic burden in the world. A promising but still unrealized goal of efforts to improve diabetes therapy is the identification of novel factors that promote pancreatic β cell (β cell) regeneration, with the long-term goal of increasing functional β cell mass in patients with either type 1 or type 2 diabetes. Reduced functional β cell mass is a central feature in both forms of the disease and in diabetes associated with obesity (Muoio, D. M., and Newgard, C. B. (2008). Mechanisms of disease: molecular and metabolic mechanisms of insulin resistance and beta-cell failure in type 2 diabetes. Nat. Rev. Mol. Cell Biol. 9, 193-205). While autoimmune destruction of β cells is the major cause of β cell loss in type 1 diabetes, a failure of β cells to compensate for ambient insulin resistance leads to uncontrolled hyperglycemia in type 2 diabetes.

Thus, what is needed are compositions and methods effective in promoting β cell proliferation, especially in subjects that are in need of improved β cell function.

SUMMARY OF THE INVENTION

Lending encouragement to therapeutic strategies aimed at enhancing β cell mass, decades of research indicate that β cells possess the capacity to compensate for both physiological (pregnancy) and pathological (obesity) insulin resistance (Ogilvie, R. F. (1933). The islands of langerhans in 19 cases of obesity. J. Pathol. Bacteriol. 37, 473-481; Van Assche, F. A., et al., (1978). A morphological study of the endocrine pancreas in human pregnancy. Br. J. Obstet. Gynaecol. 85, 818-820). Although β cell growth in both humans and rodents has been documented to occur through self-duplication of preexisting β cells (Dor, Y., et al., (2004). Adult pancreatic beta-cells are formed by self-duplication rather than stem-cell differentiation. Nature 429, 41-46; Meier, J. J., et al., (2008). Beta-cell replication is the primary mechanism subserving the postnatal expansion of beta-cell mass in humans. Diabetes 57, 1584-1594; Teta, M., et al., (2007). Growth and regeneration of adult beta cells does not involve specialized progenitors. Dev. Cell 12, 817-826), albeit at low levels, the source of putative growth factor(s) mediating this process, especially in the context of insulin resistance, remains unknown. Among possible systemic regulators of β cell mass, gut-derived incretins such as glucagon-like peptide-1 (GLP-1), glucose-dependent insulin-tropic polypeptide (GIP) (Renner, S., et al., (2010). Glucose intolerance and reduced proliferation of pancreatic beta-cells in transgenic pigs with impaired glucose-dependent insulinotropic polypeptide function. Diabetes 59, 1228-1238). Glucose intolerance and reduced proliferation of pancreatic beta-cells in transgenic pigs with impaired glucose-dependent insulinotropic polypeptide function. Diabetes 59, 1228-1238; Saxena, R., et al.; GIANT consortium; MAGIC investigators. (2010). Genetic variation in GIPR influences the glucose and insulin responses to an oral glucose challenge. Nat. Genet. 42, 142-148), adipocyte-derived adipokines including leptin (Morioka, T., et al., (2007). Disruption of leptin receptor expression in the pancreas directly affects beta cell growth and function in mice. J. Clin. Invest. 117, 2860-2868) and adiponectin (Holland, W. L., et al., (2011). Receptor-mediated activation of ceramidase activity initiates the pleiotropic actions of adiponectin. Nat. Med. 17, 55-63), muscle-derived myokines such as IL-6 (Ellingsgaard, H., et al., (2008). Interleukin-6 regulates pancreatic alpha-cell mass expansion. Proc. Natl. Acad. Sci. USA 105, 13163-13168; Suzuki, T., et al., (2011). Interleukin-6 enhances glucose-stimulated insulin secretion from pancreatic beta-cells: potential involvement of the PLC-IP3-dependent pathway. Diabetes 60, 537-547), macrophage-derived cytokines including IL-1b, IFNγ, and TNF-a (Wang, C., et al., (2010). Cytokines in the Progression of Pancreatic b-Cell Dysfunction. Int. J. Endocrinol. 2010, 515136), bone derived osteocalcin (Ferron, M., et al., (2008). Osteocalcin differentially regulates beta cell and adipocyte gene expression and affects the development of metabolic diseases in wild-type mice. Proc. Natl. Acad. Sci. USA 105, 5266-5270), thyroid-derived T3/T4 hormones (Jörns, A., et al., (2010). Beta cell mass regulation in the rat pancreas through glucocorticoids and thyroid hormones. Pancreas 39, 1167-1172; Verga Falzacappa, C., et al., (2010). The thyroid hormone T3 improves function and survival of rat pancreatic islets during in vitro culture. Islets 2, 96-103), platelet-derived growth factor (PDGF) (Chen, H., of al., (2011). PDGF signaling controls age-dependent proliferation in pancreatic b-cells. Nature 478, 349-355), serotonin (Kim, H., et al., (2010). Serotonin regulates pancreatic beta cell mass during pregnancy. Nat. Med. 16, 804-808), and FGF21 (Wente, W., et al., (2006). Fibroblast growth factor-21 improves pancreatic beta-cell function and survival by activation of extracellular signal-regulated kinase ½ and Akt signaling pathways. Diabetes 55, 2470-2478) have each been implicated. However, the lack of significant and consistent alterations in these known factors in the peripheral blood that can fully account for the β cell proliferation in the insulin-resistant LIRKO (Liver Insulin Receptor Knockout) mouse model (see, Table 1) prompted us to explore the presence of an as yet unidentified factor that is derived from an insulin-resistant liver.

TABLE 1

Assays of circulating growth factors, hormones, cytokines and chemokines in young vs. old Control and LIRKO mice

| | Control (3 Mo) | LIRKO (3 Mo) | p | Control (12 Mo) | LIRKO (12 Mo) | p |
|---|---|---|---|---|---|---|
| Growth factors | | | | | | |
| IGF1 (ng/mL) | 211.9 ± 18.9 | 68.9 ± 16.6 | 0.0002 | 525.1 ± 35.6 | 194.4 ± 18.6 | 2.91E−06 |
| HGF (ng/mL) | 5.3 ± 0.41 | 4 ± 0.69 | 0.145 | 2.1 ± 0.3 | 4.3 ± 0.8 | 0.03 |
| EGF (ng/mL) | 54.75 ± 17.33 | 79.8 ± 23.73 | 0.4 | 11.7 ± 3.1 | 14.5 ± 6.1 | 0.7 |
| PDGFAA (ng/mL) | 0.142 ± 0.05 | 0.163 ± 0.05 | 0.88 | 3.4 ± 0.4 | 3.6 ± 0.4 | 0.7 |
| PDGFBB (ng/mL) | 0.073 ± 0.02 | 0.17 ± 0.07 | 0.22 | 9 ± 1.5 | 9.8 ± 1.2 | 0.6 |
| VEGF (pg/mL) | 2.1 ± 0.2 | 1.3 ± 0.1 | 0.006 | 1.8 ± 0.3 | 2.1 ± 0.4 | 0.5 |
| FGF21 (pg/mL) | 58.6 ± 12.6 | 43.6 ± 11.1 | 0.4 | 1203 ± 224.6 | 143.2 ± 29.3 | 0.001 |
| Hormones | | | | | | |
| Insulin (ng/mL) | 2.3 ± 0.7 | 11.6 ± 2.4 | 0.01 | 8.2 ± 1 | 17.8 ± 4.4 | 0.06 |
| Amylin (pg/mL) | 103.6 ± 40.9 | 206.8 ± 51.1 | 0.1 | 358.4 ± 38 | 900.8 ± 309.6 | 0.1 |
| Glucagon (pM) | 25.8 ± 3.4 | 20.9 ± 4.8 | 0.4 | 13.1 ± 3.9 | 11.5 ± 3.8 | 0.8 |
| Ghrelin (pg/mL) | 3.5 ± 0.5 | 2.5 ± 0.4 | 0.1 | 1.7 ± 0 | 4.5 ± 1.9 | 0.2 |
| PP (pg/mL) | 11.8 ± 2.9 | 19.7 ± 4 | 0.1 | 18 ± 4.8 | 42.2 ± 17.4 | 0.2 |
| PYY (pg/mL) | 63.1 ± 12 | 74.8 ± 13 | 0.5 | 145.9 ± 38.3 | 86.7 ± 7.6 | 0.2 |
| GIP (pg/mL) | 108.5 ± 11.4 | 152.9 ± 18.7 | 0.06 | 284.5 ± 25 | 95.2 ± 13.9 | 2.1E−05 |
| Total GLP-1 (pg/mL) | 32.1 ± 5 | 43.6 ± 11.6 | 0.4 | 59.4 ± 11.4 | 65.9 ± 17.9 | 0.7 |
| Active GLP-1 (pg/mL) | 23.8 ± 7.4 | 22.5 ± 6.3 | 0.9 | 25.5 ± 7.6 | 27.7 ± 9.8 | 0.8 |
| Leptin (ng/mL) | 12.3 ± 4 | 8.9 ± 1.7 | 0.4 | 42.9 ± 6.2 | 27.7 ± 1.7 | 0.04 |
| Resistin (ng/mL) | 2.4 ± 0.2 | 2.7 ± 0.2 | 0.3 | 1.3 ± 0.1 | 1.5 ± 0.1 | 0.2 |
| Adiponectin (μg/mL) | 10.9 ± 1.4 | 17.5 ± 2.6 | 0.04 | 21.2 ± 2.3 | 18.8 ± 1.3 | 0.4 |
| Osteopontin (ng/mL) | 146.2 ± 8.1 | 157.1 ± 24.6 | 0.7 | 161.3 ± 16.9 | 232.1 ± 20.5 | 0.01 |
| Osteocalcin (ng/mL) | 12.6 ± 1.2 | 12.6 ± 2.9 | 1 | 11.8 ± 2.2 | 12.9 ± 2.7 | 0.8 |
| Gastrin (pg/mL) | 39.4 ± 2.3 | 43.1 ± 4.6 | 0.5 | 45.7 ± 6.2 | 40.9 ± 5.9 | 0.6 |
| Cytokines & Chemokines | | | | | | |
| IL-1a (pg/mL) | 12.4 ± 2.7 | 14.3 ± 6.4 | 0.8 | 9.4 ± 3.6 | 21.2 ± 8.4 | 0.2 |
| IL-1b (pg/mL) | 6.6 ± 2.9 | 3.2 ± 0.6 | 0.3 | 3.3 ± 0.4 | 5.8 ± 2.5 | 0.3 |
| IL-2 (pg/mL) | 1.4 ± 0.1 | 1.2 ± 0.05 | 0.1 | 1.3 ± 0.3 | 1.5 ± 0.2 | 0.6 |
| IL-3 (pg/mL) | 1.4 ± 0.07 | 1.3 ± 0.1 | 0.6 | 1.4 ± 0 | 2.36 ± 1 | 0.3 |
| IL-4 (pg/mL) | 0.7 ± 0.04 | 0.9 ± 0.2 | 0.4 | 0.8 ± 0.35 | 0.5 ± 0.04 | 0.4 |
| IL-5 (pg/mL) | 7.3 ± 1.8 | 8.3 ± 2.1 | 0.7 | 2.7 ± 1.2 | 1.9 ± 0.9 | 0.6 |
| IL-6 (pg/mL) | 3.4 ± 1.4 | 2.8 ± 1.6 | 0.7 | 27.8 ± 3.4 | 19.4 ± 2.3 | 0.06 |
| IL-7 (pg/mL) | 1.4 ± 0.2 | 3.5 ± 1.8 | 0.2 | 17.5 ± 9.1 | 15 ± 9.8 | 0.8 |
| IL-9 (pg/mL) | 13.8 ± 4.2 | 9.1 ± 2.9 | 0.4 | 3.5 ± 1 | 7.9 ± 4.3 | 0.3 |
| IL-10 (pg/mL) | 11.8 ± 1.4 | 9.7 ± 1.6 | 0.3 | 11.2 ± 2.5 | 12.8 ± 3.5 | 0.7 |
| IL-12(P40) (pg/mL) | 16.7 ± 2.5 | 10.2 ± 2.5 | 0.08 | 6.3 ± 2.2 | 4.3 ± 1 | 0.4 |
| IL-12 (p70) (pg/mL) | 10.5 ± 2.6 | 9.3 ± 2.9 | 0.7 | 10.2 ± 7.3 | 6.3 ± 2.1 | 0.6 |
| IL-13 (pg/mL) | 103.4 ± 12.7 | 84.6 ± 14.6 | 0.3 | 83.8 ± 12.7 | 134.1 ± 33.2 | 0.2 |
| IL-15 (pg/mL) | 7.7 ± 2.2 | 12.5. ± 7 | 0.5 | 35.7 ± 18 | 48 ± 29.4 | 0.7 |
| IL-17 (pg/mL) | 1.3 ± 0.2 | 0.9 ± 0.3 | 0.2 | 2.5 ± 1 | 1.4 ± 0.3 | 0.3 |
| IFN-g (pg/mL) | 2.9 ± 0.6 | 2 ± 0.2 | 0.2 | 3 ± 2.1 | 1.1 ± 0.2 | 0.4 |
| TNF-a (pg/mL) | 2.4 ± 0.5 | 2 ± 0.5 | 0.5 | 2.9 ± 0.08 | 4.7 ± 1.6 | 0.3 |
| PAI-1 (ng/mL) | 1.4 ± 0.2 | 1.3 ± 0.1 | 0.5 | 1.6 ± 0.3 | 1.3 ± 0.3 | 0.3 |
| G-CSF (pg/mL) | 217.6 ± 40.7 | 120.6 ± 25 | 0.06 | 243.8 ± 51.9 | 169.1 ± 41.5 | 0.3 |
| GM-CSF (pg/mL) | 12.7 ± 3.4 | 11.2 ± 4.3 | 0.8 | ND | ND | ND |
| M-CSF (pg/mL) | 10.3 ± 3.4 | 4.4 ± 1.2 | 0.1 | 5.2 ± 3 | 5.3 ± 2.5 | 1 |
| KC (pg/mL) | 84.1 ± 24.7 | 91.8 ± 11.8 | 0.8 | 47.2 ± 10.3 | 37.4 ± 8.7 | 0.5 |
| IP-10 (pg/mL) | 92.8 ± 10.6 | 68.9 ± 9.5 | 0.1 | 178.8 ± 20.5 | 167.3 ± 15 | 0.6 |
| Eotaxin (pg/mL) | 344.6 ± 23.4 | 342.4 ± 39.4 | 1 | 295.8 ± 19.1 | 337.1 ± 42 | 0.4 |
| MCP-1 (pg/mL) | 9.9 ± 1.8 | 5.4 ± 0.8 | 0.04 | 3.9 ± 0.4 | 5.8 ± 2.4 | 0.5 |
| MIP-1a (pg/mL) | 16.3 ± 4 | 11 ± 3.9 | 0.3 | 11.6 ± 2.8 | 7.9 ± 3.6 | 0.4 |
| MIP-1b (pg/mL) | 24.8 ± 4.7 | 13.6 ± 4 | 0.08 | 17.6 ± 5.2 | 14.3 ± 5.1 | 0.6 |
| MIP-2 (pg/mL) | 6.07 ± 1.5 | 6.07 ± 1.5 | 0.9 | ND | ND | ND |
| MIG (pg/mL) | 131.3 ± 18.6 | 129 ± 18.7 | 0.9 | 156.3 ± 28.3 | 108.5 ± 17.1 | 0.2 |
| RANTES (pg/mL) | 13.9 ± 1.7 | 10.3 ± 3 | 0.3 | 5.5 ± 1.4 | 11.9 ± 2.1 | 0.03 |
| LIX (ng/mL) | 0.9 ± 0.3 | 0.7 ± 0.2 | 0.7 | 0.3 ± 0.1 | 0.4 ± 0.1 | 0.7 |

Integrative organ crosstalk regulates key aspects of energy homeostasis, and its dysregulation may underlie metabolic disorders such as obesity and diabetes. To test the hypothesis that crosstalk between the liver and pancreatic islets modulates β cell growth in response to insulin resistance, we used the liver-specific insulin receptor knockout (LIRKO) mouse, a unique model that exhibits dramatic islet hyperplasia. Using complementary in vivo parabiosis and transplantation assays, as well as in vitro islet culture approaches, we demonstrate that humoral, nonneural, non-cell-autonomous factor(s) induces β cell proliferation in LIRKO mice.

Furthermore, we have discovered that a hepatocyte-derived factor(s) stimulates mouse and human β cell proliferation in ex vivo assays, independent of ambient glucose and insulin levels. These data implicate the liver as a critical source of β cell growth factor(s) in insulin-resistant states.

Serine peptidase inhibitor B1 (SerpinB1) is a 42 kD protein known to regulate the activity of the neutrophil proteases, elastase, cathrpsin G, proteinase-3, chymase, chymotrypsin and kallikrein-3. Thus, the role of SerpinB1 is presumably assigned to cellular proteolysis. In the present invention SerpinB1 was identified as a top candidate β-cell growth factor by Affymetrix analysis and Proteomics screening using serum, LCM and HCM samples from the LIRKO mouse. This finding is supported by data from our recent study pointing to a serum factor as a potential pro-proliferative candidate. Furthermore, we confirmed with ELISA assays that the circulating levels of SerpinB1 were upregulated in LIRKO serum. To directly test the effects of SerpinB1 in β-cell proliferation Sivelestat (a SerpinB1 functional analog; i.e., a pharmacological mimicker of SerpinB1 activity) and Serpin B1 are used. A direct effect of Sivelestat and SerpinB1 was shown in the promotion of β-cell proliferation in vivo and in vitro in a dose-dependent manner.

Earlier observations were made regarding the possible "indirect" role of SerpinB1 in β-cell physiology. SerpinB1 mRNA level was demonstrated to be commonly increased in regenerating pancreas of mice administrated with Exendin-4 or subjected to partial pancreatectomy. These data suggested SerpinB1 activity correlated with β-cell proliferation induced by Exendin-4 and after partial removal of pancreas (see, De León, et al., Identification of transcriptional targets during pancreatic growth after partial pancreatectomy and exendin-4 treatment. *Physiol Genomics*. 2006, 24:133-143). The importance of SerpinB1 in β-cell biology was also described using a chip on chip approach. It was further reported that the β-cell transcription factor pdx-1 binds to the proximal promoter of SerpinB1 locus, suggesting a possible role for SerpinB1 in mediating pdx-1 effects in pancreatic β-cells (see, Sachdeva, et al., Pdx1 (MODY4) regulates pancreatic beta cell susceptibility to ER stress. *PNAS*. 2009, 106(45):19090-19095). However, these workers did not show the involvement of SerpinB1 in β cell proliferation and do not provide the suggestion or motivation for investigating this direction.

The invention relates to further embodiments which are outlined as follows:

In one embodiment the present invention relates to the use of a Serpin peptide or active fragment, or an analog thereof as medicament.

In another embodiment it relates to said use, wherein said Serpin peptide is SerpinB1.

In yet another embodiment it relates to said use, wherein said Serpin analog is a known functional analog.

In yet another embodiment it relates to said use, wherein said Serpin analog is a known structural analog.

In a further embodiment it relates to said use, wherein the subject has diabetes.

In yet a further embodiment it relates to said use, wherein the subject is at risk of developing diabetes.

In another aspect of the present invention it relates to a Serpin peptide or active fragment, or an analog thereof for improving the β cell function in a subject.

In another embodiment it relates to said peptide or active fragment, or said analog thereof, wherein said Serpin peptide is SerpinB1.

In yet another embodiment it relates to said peptide or active fragment, or said analog thereof, wherein said Serpin analog is a known functional analog.

In a further embodiment it relates to said peptide or active fragment, or said analog thereof, wherein said Serpin analog is a known structural analog.

In even a further embodiment it relates to said peptide or active fragment, or said analog thereof, wherein the subject has diabetes.

In yet even a further embodiment it relates to said peptide or active fragment, or said analog thereof, wherein the subject is at risk of developing diabetes.

In another aspect of the present invention it relates to a Serpin peptide or active fragment, or an analog thereof for promoting pancreatic β cell proliferation in a subject.

In another embodiment it relates to said peptide or active fragment, or said analog thereof, wherein said Serpin peptide is SerpinB1.

In yet another embodiment it relates to said peptide or active fragment, or said analog thereof, wherein said population of pancreatic β cells are in vivo.

In another embodiment it relates to said peptide or active fragment, or said an analog thereof, wherein said population of pancreatic β cells are in vitro.

In a further embodiment it relates to said peptide or active fragment, or said analog thereof, wherein said Serpin analog is a known functional analog.

In yet a further embodiment it relates to said peptide or active fragment, or said analog thereof, wherein said Serpin analog is a known structural analog.

In yet a further embodiment it relates to said peptide or active fragment, or said analog thereof, wherein increased pancreatic β cell proliferation in vivo is indicated by detecting increased glycemic control in the subject.

In another aspect of the present invention it relates to an expression construct encoding a Serpin peptide or active fragment, or analog thereof for improving the β cell function in a subject.

In one embodiment it relates to said expression construct encoding a Serpin peptide or active fragment, or said analog thereof, wherein said encoded Serpin peptide is SerpinB1.

In another embodiment it relates to said expression construct encoding a Serpin peptide or active fragment, or said analog thereof, wherein said encoded Serpin peptide analog is a known functional analog.

In yet another embodiment it relates to said expression construct encoding a Serpin peptide or active fragment, or said analog thereof, wherein said encoded Serpin peptide analog is a known structural analog.

In a further embodiment it relates to said expression construct encoding a Serpin peptide or active fragment, or said analog thereof, wherein the subject has diabetes.

In yet a further embodiment it relates to said expression construct encoding a Serpin peptide or active fragment, or analog thereof, wherein the subject is at risk of developing diabetes.

In yet a further embodiment it relates to said use of a Serpin peptide or active fragment, or an analog thereof for manufacturing of a medicament for improving the β cell function in a subject.

Another aspect of the present invention relates to the before mentioned use, wherein said Serpin peptide is SerpinB1.

Yet another aspect of the present invention relates to the before mentioned use, wherein said Serpin analog is a known functional analog.

Yet another aspect of the present invention relates to the before mentioned use, wherein said Serpin analog is a known structural analog.

Yet another aspect of the present invention relates to the before mentioned use, wherein the subject has diabetes.

Yet another aspect of the present invention relates to the before mentioned use, wherein the subject is at risk of developing diabetes.

Another aspect of the present invention relates to the use of a Serpin peptide or active fragment, or an analog thereof for manufacturing of a medicament for promoting pancreatic β cell proliferation in a subject.

In one embodiment it relates to said use, wherein said Serpin peptide is SerpinB1. In another embodiment it relates to said use, wherein said population of pancreatic β cells are in vivo.

In yet another embodiment it relates to said use, wherein said population of pancreatic β cells are in vitro.

In a further embodiment it relates to said use, wherein said Serpin analog is a known functional analog.

In a further embodiment it relates to said use, wherein said Serpin analog is a known structural analog.

In a further embodiment it relates to said use, wherein increased pancreatic β cell proliferation in vivo is indicated by detecting increased glycemic control in the subject.

Another aspect of the present invention relates to the use of an expression construct encoding a Serpin peptide or active fragment, or analog thereof for manufacturing of a medicament for improving the β cell function in a subject.

In one embodiment it relates to said use, wherein said encoded Serpin peptide is SerpinB1.

In another embodiment it relates to said use, wherein said encoded Serpin peptide analog is a known functional analog.

In yet another embodiment it relates to said use, wherein said encoded Serpin peptide analog is a known structural analog.

In yet another embodiment it relates to said use, wherein the subject has diabetes.

In yet another embodiment it relates to said use, wherein the subject is at risk of developing diabetes.

BRIEF DESCRIPTION OF THE FIGURES

FIG. 13 shows an exemplary nucleotide sequence for murine SerpinB1 (SEQ ID NO: 1).

FIG. 14 shows an exemplary nucleotide sequence for human SerpinB1 (SEQ ID NO: 2).

FIGS. 16(A & B) shows identification of mouse SerpinB1 by LC-MS analysis. A) shows the tryptic peptides of mouse SerpinB1 (mouse SerpinB1 is designated SEQ ID NO: 3) identified by LC/MSMS (highlighted). B) shows proteomic analysis of HCM from LIRKO mice.

DETAILED DESCRIPTION OF THE INVENTION

Figure 1:
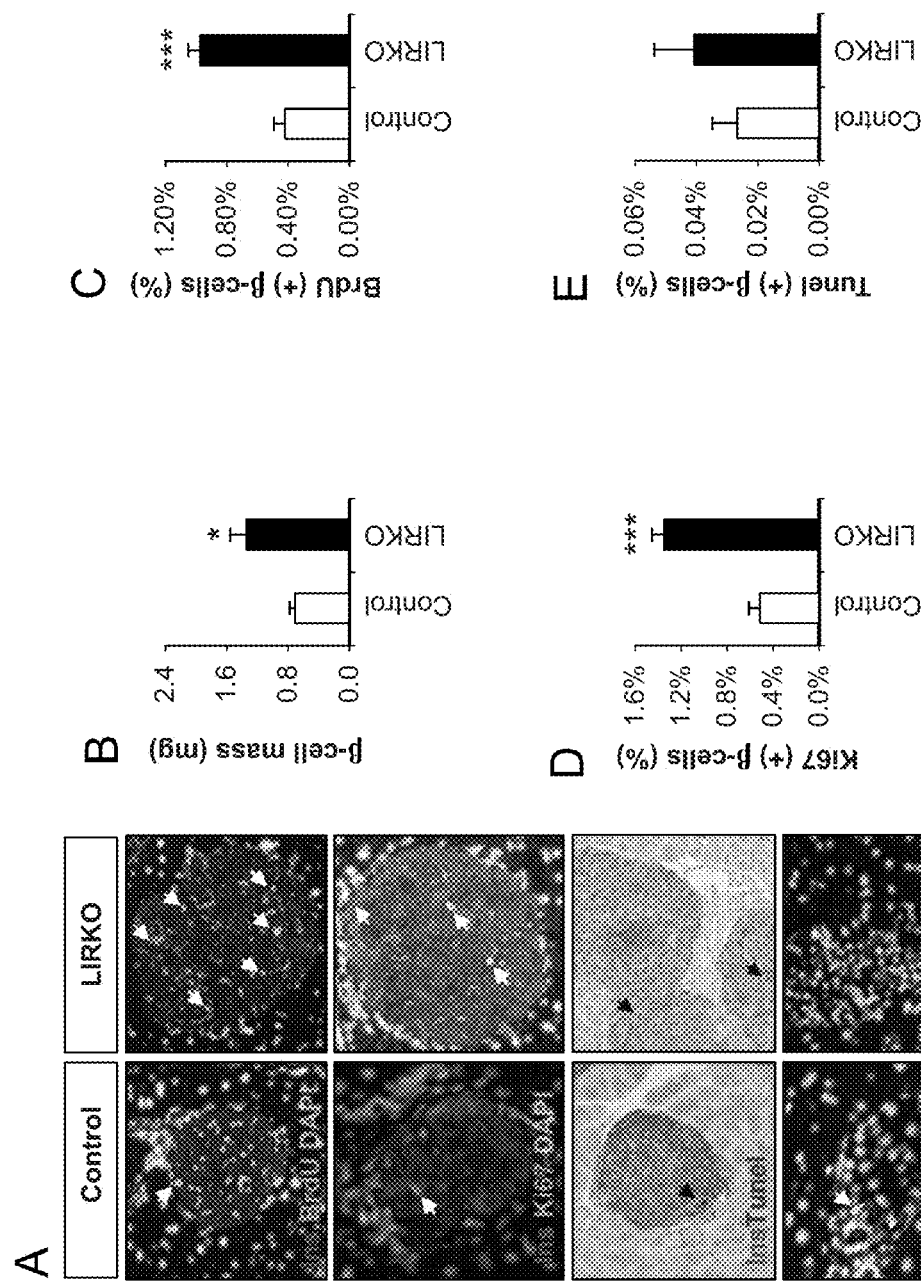
FIG. 1(A-H) shows selective β cell proliferation in LIRKO mice. Three to 4-month-old LIRKO and control mice were intraperitoneally injected with BrdU (100 mg/kg body weight) 5 hr before animals were sacrificed, and tissues were dissected, fixed and stained as indicated. (A) Pancreatic sections immunostained for insulin/BrdU/DAPI, insulin/Ki67/DAPI, insulin/TUNEL, or glucagon/BrdU/DAPI as indicated. (B) β cell mass quantification. (C and D) Quantification of BrdU+ insulin+ and Ki67+ insulin+ cells: between 2,000 and 5,000 insulin+ cells per animal were counted in control versus LIRKO pancreases, respectively. (E) Quantification of TUNEL+ insulin+ cells: between 2,000 and 5,000 insulin+ cells/mouse were counted in control versus LIRKO pancreases, respectively. (F) Quantification of BrdU+ glucagon+ cells: between 2,000 and 5,000 insulin+ cells/mouse were counted in control versus LIRKO pancreases, respectively. (G) Quantification of nuclei BrdU+ in indicated tissues: 4,000-5,000 cells/mouse were counted in each of liver, kidney, spleen, and lung, and 1,500 cells/mouse were counted in each for visceral (Visc.) and subcutaneous (Sc.) adipose tissue and skeletal muscle (Sk). (H) Representative images of proliferating cells in tissue sections stained with BrdU. Data represent mean±SEM. *p % 0.05 and ***p % 0.001 (n=6 in each group). See also FIG. 6 and Table 2.
Figure 1:
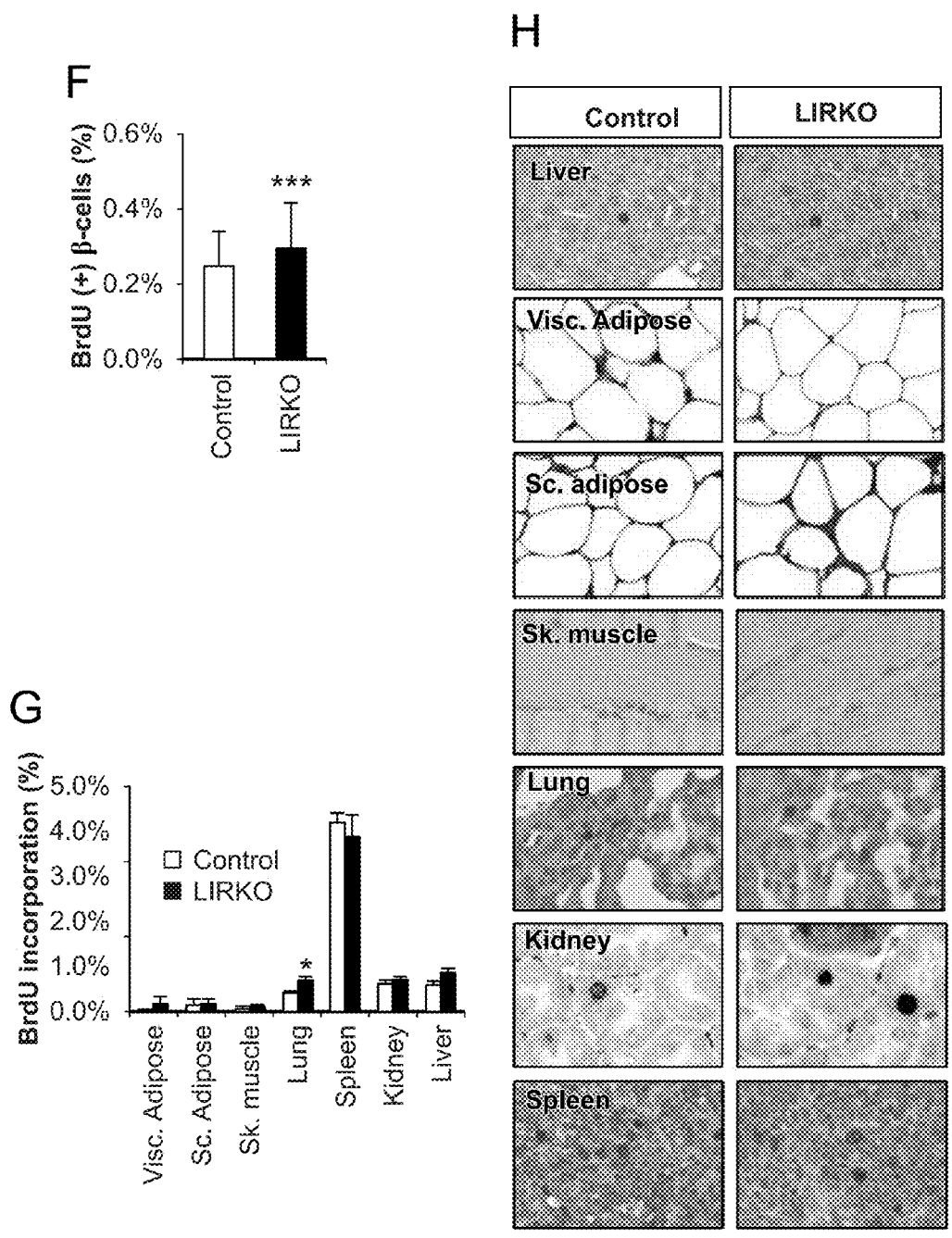

Serpins (serine protease inhibitors) are a superfamily of ~45 kDa (kD) proteins with a highly conserved tertiary structure. Serpins regulate important intracellular and extracellular proteolytic events, including apoptosis, complement activation, fibrinolysis and blood coagulation. A review of Serpins known to those of ordinary skill in the art is provided in: Benarafa, et al., Characterization of Four Murine Homologs of the Human ov-serpin Monocyte Neurophil Elastase Inhibitor MNE1 (SERPINB1), 2002, J. Biol Chem., 277(44):42028-42033, which is incorporated herein by reference. Other Serpins and serpin analogs are also know to those of ordinary skill in the art and reference to them can be found at, for example, www.ncbi.nlm.nih.gov/pubmed/ and other suitable databases.

Further, as used herein, the term "Serpin family" denotes a family of serine proteinase inhibitors which are similar in amino acid sequence and mechanism of inhibition, but may differ in their specificity toward proteolytic enzymes. This family includes, for example, alpha 1-antitrypsin (A1-Pi), angiotensinogen, ovalbumin, antiplasmin, alpha 1-antichymotrypsin, thyroxine-binding protein, complement 1 inactivators, antithrombin III, heparin cofactor II, plasminogen inactivators, gene Y protein, placental plasminogen activator inhibitor, and barley Z protein. Some members of the Serpin family may be substrates rather than inhibitors of serine endopeptidases, and some serpins occur in plants where their function is not known. See, for example, US Patent Publication No. 20120195859 and references therein, all of which are incorporated herein by reference.

The term "cellular proliferation" and "cell proliferation" refer to an increase in the number of cells as a result of cell growth and cell division. Cell or cellular proliferation may include the inducement of cell division by resting cells or senescent cells and may include the increase in the rate of cell division of cells already undergoing cell division.

The methods described herein include the manufacture and use of pharmaceutical compositions, which include compounds identified by a method described herein as active ingredients. Also included are the pharmaceutical compositions themselves.

Pharmaceutical compositions typically include a pharmaceutically acceptable carrier. As used herein the language "pharmacological composition," "pharmacological carrier" or "pharmaceutically acceptable carrier" includes compositions and carriers comprising one or more of, for example, saline, solvents, dispersion media, coatings, antibacterial and antifungal agents, isotonic and absorption delaying agents, buffers and the like, compatible with pharmaceutical administration. Supplementary active compounds can also be incorporated into the compositions. Suitable pharmaceutical compositions and carriers are also defined herein to include compositions and carriers suitable for in vitro use, e.g., for diagnostic use, research use and ex vivo manipulation of cells and tissues.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known to one of ordinary skill in the art, see, e.g., the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use can include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile or capable of being sterilized and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL® (sodium starch glycollate), or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798, which is incorporated herein by reference.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art, or into adhesive pads, as is generally known in the art.

The pharmaceutical compositions can also be prepared in the form of suppositories (e.g., with conventional suppository bases such as cocoa butter and other glycerides) or retention enemas for rectal delivery.

Therapeutic compounds that are or may include nucleic acids (i.e., a nucleic acid encoding one or more of the Serpins or a Serpin analog of the present invention) can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587, which are incorporated herein by reference. Additionally, intranasal delivery is possible, as described in, inter alia, Hamajima et al., Clin. Immunol. Immunopathol. 88(2), 205-10 (1998). Liposomes (e.g., as described in U.S. Pat. No. 6,472,375, which is incorporated herein by reference) and microencapsulation can also be used. Biodegradable targetable microparticle delivery systems can also be used (e.g., as described in U.S. Pat. No. 6,471,996, which is incorporated herein by reference).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques as are known to one of ordinary skill in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, which is incorporated herein by reference.

The pharmaceutical compositions can be included in a kit, container, pack or dispenser together with instructions for administration.

Methods of Treatment

The methods described herein include methods for the treatment of disorders associated with impaired glucose tolerance, e.g., for the improvement of glycemic control and insulin sensitivity by promoting β cell proliferation. In some embodiments, the disorder is type 1 or type 2 diabetes. Generally, the methods include administering a therapeutically effective amount of therapeutic compound as described herein, to a subject who is in need of, or who has been determined to be in need of, such treatment.

As used in this context, to "treat" means to ameliorate at least one symptom of the disorder associated with impaired glucose tolerance. Often, impaired glucose tolerance results in hyperglycemia; thus, a treatment can result in a return or approach to normoglycemia/normal insulin sensitivity. As used in this context, to "prevent diabetes," "prevent type 1 diabetes" or "prevent type 2 DM" (i.e., type 2 diabetes mellitus), or similar, means to reduce the likelihood that a subject will develop diabetes, type 1 diabetes or type 2 DM, respectively. One of skill in the art will appreciate that a preventive treatment is not required to be 100% effective, but can instead result in a delay in the onset of T1 D, T2DM, or a reduction in symptoms, e.g., an improvement in glucose tolerance.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount," "therapeutic amount" or "sufficient amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The pharmaceutical compositions can be included in a container, pack, or dispenser together with instructions for administration.

In some embodiments, the pharmaceutical composition is injected into a tissue, e.g., pancreatic tissue or liver tissue.

Serpin Nucleic Acids

The nucleic acid molecules encoding the peptides described herein (for example, the sequences of FIGS. 13 and 14, or portions thereof) can be inserted into vectors and used as expression vectors and as gene therapy vectors. Other Serpin sequences are known to those of skill in the art and can be found, for example, at www.ncbi.nlm.nih.gov/pubmed/ and similar databases. The construction of suitable, functional expression constructs and expression vectors is known to one of ordinary skill in the art. In an embodiment of the present invention, expression of the Serpin peptide is directed towards the open reading frame of the sequences given in FIGS. 13 and 14 (see, for example, GenBank sequence nos. NM_030666.3 and NM_025429.2). One of ordinary skill in the art will be able to detect active fragments without undue experimentation by, for example, cleavage of the peptide into fragments and testing the fragments for activity in in vivo and in vitro assays, as are exemplified below. Similarly, constructs expressing Serpin fragments can be transfected into primary and cultured cell lines suitable for responding to Serpin activity or in vivo model systems, as are known to those of ordinary skill in the art, some of which are exemplified below. One of ordinary skill in the art, knowledgeable of protein secondary, tertiary and quaternary structures and protein function, will be able to identify protein fragments suitable for testing.

Gene therapy vectors can be delivered to a subject by, for example, intravenous injection, local administration (see U.S. Pat. No. 5,328,470) or by stereotactic injection (see, e.g., Chen et al., PNAS 91:3054-3057 (1994)). The pharmaceutical preparation of the gene therapy vector can include the gene therapy vector in an acceptable diluent, or can include a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system. Further, antisense nucleic acids, short interfering RNA (siRNA), interfering RNA (RNAi) and micro- RNA (miRNA) can be used to regulate expression of target Serpin genes and associated regulatory peptides. Antisense technology, RNAi, siRNA and miRNA technology is known by and can be practiced by those of ordinary skill in the art.

Serpins (e.g., SerpinB1) are known to exist in the plasma making them promising candidates as a biomarker. Serpins can be used as biomarkers in view of the teachings of the present invention to, for example, monitor treatments that affect β cell proliferation and diabetes. The compositions disclosed herein can include agents that detect or bind (e.g., that detect or bind specifically) to a biomarker described herein (e.g., one or more Serpins and members of the Serpin family, as described herein). Such agents can include, but are not limited to, for example, antibodies, antibody fragments, peptides and known small molecule agents. In some instances, the compositions can be in the form of a kit. Such kits can include one or more agents that can detect or bind (e.g., that detect or bind specifically) to one or more biomarkers described herein and instructions for use.

Gene Therapy

The nucleic acids described herein, e.g., an antisense nucleic acid described herein, or a Serpin (e.g., SerpinB1) polypeptide encoding nucleic acid, can be incorporated into a gene construct to be used as a part of a gene therapy protocol to deliver nucleic acids encoding either an agonistic or antagonistic form of an agent described herein, e.g., a Serpin (e.g., SerpinB1), or an active fragment thereof or a functional or structural analog thereof. The invention features expression vectors for in vivo transfection and expression of e.g., a Serpin polypeptide (e.g., SerpinB1) or an active fragment thereof or a functional or structural analog thereof, described herein. Expression constructs of such components may be administered in any biologically effective carrier, e.g., any formulation or composition capable of effectively delivering the component gene to cells in vivo, as are known to one of ordinary skill in the art. Approaches include insertion of the subject gene in viral vectors including recombinant retroviruses, adenovirus, adeno-associated virus and herpes simplex virus-1, or recombinant bacterial or eukaryotic plasmids. Viral vectors transfect cells directly; plasmid DNA can be delivered with the help of, for example, cationic liposomes (e.g., LIPOFECTIN™) or derivatized (e.g., antibody conjugated), polylysine conjugates, gramicidin S, artificial viral envelopes or other such intracellular carriers, as well as direct injection of the gene construct or $CaPO_4$ precipitation carried out in vivo, as is known to one of ordinary skill in the art.

One approach for in vivo introduction of nucleic acid into a cell is by use of a viral vector containing nucleic acid, e.g., a cDNA, encoding an alternative pathway component described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see, e.g., Miller, Blood 76:271-78 (1990)). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, et al., (eds.) Greene Publishing Associates, (1989), Sections 9.10-9.14, and other standard laboratory manuals. Non-limiting examples of suitable retroviruses include pLJ, pZIP, pWE and pEM which are known to those of ordinary skill in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see, for example, Eglitis, et al., Science 230:1395-1398 (1985); Danos and Mulligan, Proc. Natl. Acad. Sci. USA 85:6460-6464 (1988); Wilson, et al., Proc. Natl. Acad. Sci. USA 85:3014-3018 (1988); Armentano, et al., Proc. Natl. Acad. Sci. USA 87:6141-6145 (1990); Huber, et al., Proc. Natl. Acad. Sci. USA 88:8039-8043 (1991); Ferry, et al., Proc. Natl. Acad. Sci. USA 88:8377-8381 (1991); Chowdhury, et al., Science 254:1802-1805 (1991); van Beusechem, et al., Proc. Natl. Acad. Sci. USA 89:7640-7644 (1992); Kay, et al., Human Gene Therapy 3:641-647 (1992); Dai, et al., Proc. Natl. Acad. Sci. USA 89:10892-10895 (1992); Hwu, et al., J. Immunol. 150:4104-4115 (1993); U.S. Pat. No. 4,868,116; U.S. Pat. No. 4,980,286; PCT Application WO 89/07136; PCT Application WO 89/02468; PCT Application WO 89/05345; and PCT Application WO 92/07573; all of which are incorporated herein by reference in their entirety).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner, et al., BioTechniques 6:616 (1988); Rosenfeld, et al., Science 252:431-434 (1991); and Rosenfeld, et al., Cell 68:143-155 (1992). Suitable adenoviral vectors derived from the adenovirus strain Ad type 5 dl324 or other strains of adenovirus (e.g., Ad2, Ad3, Ad7 etc.) are known to those of ordinary skill in the art. Recombinant adenoviruses can be advantageous in certain circumstances in that they are not capable of infecting non-dividing cells and can be used to infect a wide variety of cell types, including epithelial cells (Rosenfeld, et al. (1992), supra). Furthermore, the virus particle is relatively stable and amenable to purification and concentration and, as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner, et al. (1998), supra; Haj-Ahmand and Graham, J. Virol. 57:267 (1986)).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka, et al., Curr. Topics in Micro. and Immunol. 158:97-129 (1992)). It is also one of the few viruses that may integrate its DNA into non-dividing cells, and exhibits a high frequency of stable integration (see for example Flotte, et al., Am. J. Respir. Cell. Mol. Biol. 7:349-356 (1992); Samulski, et al., J. Virol. 63:3822-3828 (1989); and McLaughlin, et al., J. Virol. 62:1963-1973 (1989)). Vectors containing as little as 300 base pairs of MV can be packaged and can integrate. Space for exogenous DNA is limited to about 4.5 kb. An AAV vector such as that described in Tratschin, et al., Mol. Cell. Biol. 5:3251-3260 (1985) can be used to introduce DNA into cells. A variety of nucleic acids have been introduced into different cell types using AAV vectors (see for example Hermonat, et al., Proc. Natl. Acad. Sci. USA 81:6466-6470 (1984); Tratschin, et al., Mol. Cell. Biol. 4:2072-2081 (1985); Wondisford, et al., Mol. Endocrinol. 2:32-39 (1988); Tratschin, et al., J. Virol. 51:611-619 (1984); and Flotte, et al., J. Biol. Chem. 268:3781-3790 (1993)).

In addition to viral transfer methods, such as those illustrated above, non-viral methods can also be employed to cause expression of an nucleic acid agent described herein (e.g., a Serpin (e.g., SerpinB1), an active fragment thereof or a functional or structural analog thereof polypeptide encoding nucleic acid) in the tissue of a subject. Most nonviral methods of gene transfer rely on normal mechanisms used by mammalian cells for the uptake and intracellular transport of macromolecules. In some embodiments, non-viral gene delivery systems of the present invention rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli, et al., J. Invest. Dermatol. 116 (1):131-135 (2001); Cohen, et al., Gene Ther 7 (22):1896-905 (2000); or Tam, et al., Gene Ther. 7 (21):1867-74 (2000).

In a representative embodiment, a gene encoding a Serpin peptide described herein can be entrapped in liposomes bearing positive charges on their surface (e.g., lipofectins) and (optionally) which are tagged with antibodies against cell surface antigens of the target tissue (Mizuno, et al., No Shinkei Geka 20:547-551 (1992); PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g., by intravenous injection. Specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see, U.S. Pat. No. 5,328,470) or by stereotactic injection (e.g., Chen, et al., PNAS 91: 3054-3057 (1994)).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g., retroviral vectors, the pharmaceutical preparation can comprise one or more cells which produce the gene delivery system.

Cell Therapy

An agent described herein suitable for, for example, improving pancreatic β cell function or increase pancreatic β cell proliferation, e.g., a Serpin (e.g., SerpinB1), or an active fragment thereof or a functional or structural analog thereof, can also be increased in a subject by introducing into a cell, e.g., a pancreatic β cell, a nucleotide sequence that encodes a Serpin (e.g., SerpinB1), or an active fragment thereof or a functional or structural analog thereof. The nucleotide sequence can include a promoter sequence, e.g., a promoter sequence from a Serpin gene or from another gene; an enhancer sequence, e.g., 5' untranslated region (UTR), e.g., a 5' UTR, a 3' UTR; a polyadenylation site; an insulator sequence; or another sequence that modulates the expression of a Serpin (e.g., SerpinB1), or an active fragment thereof or a functional or structural analog thereof. The cell can then be introduced into the subject by methods know to one of ordinary skill in the art.

Primary and secondary cells to be genetically engineered can be obtained from a variety of tissues and include cell types which can be maintained and propagated in culture. For example, primary and secondary cells include adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient). The preferred cell for the compositions and methods of the present invention is a pancreatic β cell(s) or a liver cell(s).

The term "primary cell" includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding a Serpin (e.g., SerpinB1), or an active fragment thereof or a functional or structural analog thereof, and produce the encoded product stably and reproducibly in vitro and in vivo, over extended periods of time (i.e., hours, days, weeks or longer). A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No. 5,641,670, the contents of which are incorporated herein by reference. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electroporation, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used. Preferred sites for introduction are the pancreas or the liver. Once implanted in individual, the transfected cells produce the product encoded by the heterologous DNA or are affected by the heterologous DNA itself. For example, an individual who suffers from disease related to impaired pancreatic β cell function is a candidate for implantation of cells producing an agent described herein, e.g., a Serpin (e.g., SerpinB1), or an active fragment thereof or a functional or structural analog or mimic thereof as described herein or known to those of ordinary skill in the art.

An immunosuppressive agent, e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed, et al., N. Engl. J. Med. 327:1549 (1992); Spencer, et al., N. Engl. J. Med. 327:1541 (1992); Widner, et al., N. Engl. J. Med. 327:1556 (1992)). Dosage values may vary according to factors such as the disease state, age, sex, and weight of the individual.

All references cited herein are incorporated herein by reference in their entirety and are representative of what one of ordinary skill in the art knew at the time of the present invention.

EXEMPLIFICATION

Example 1

Figure 6:
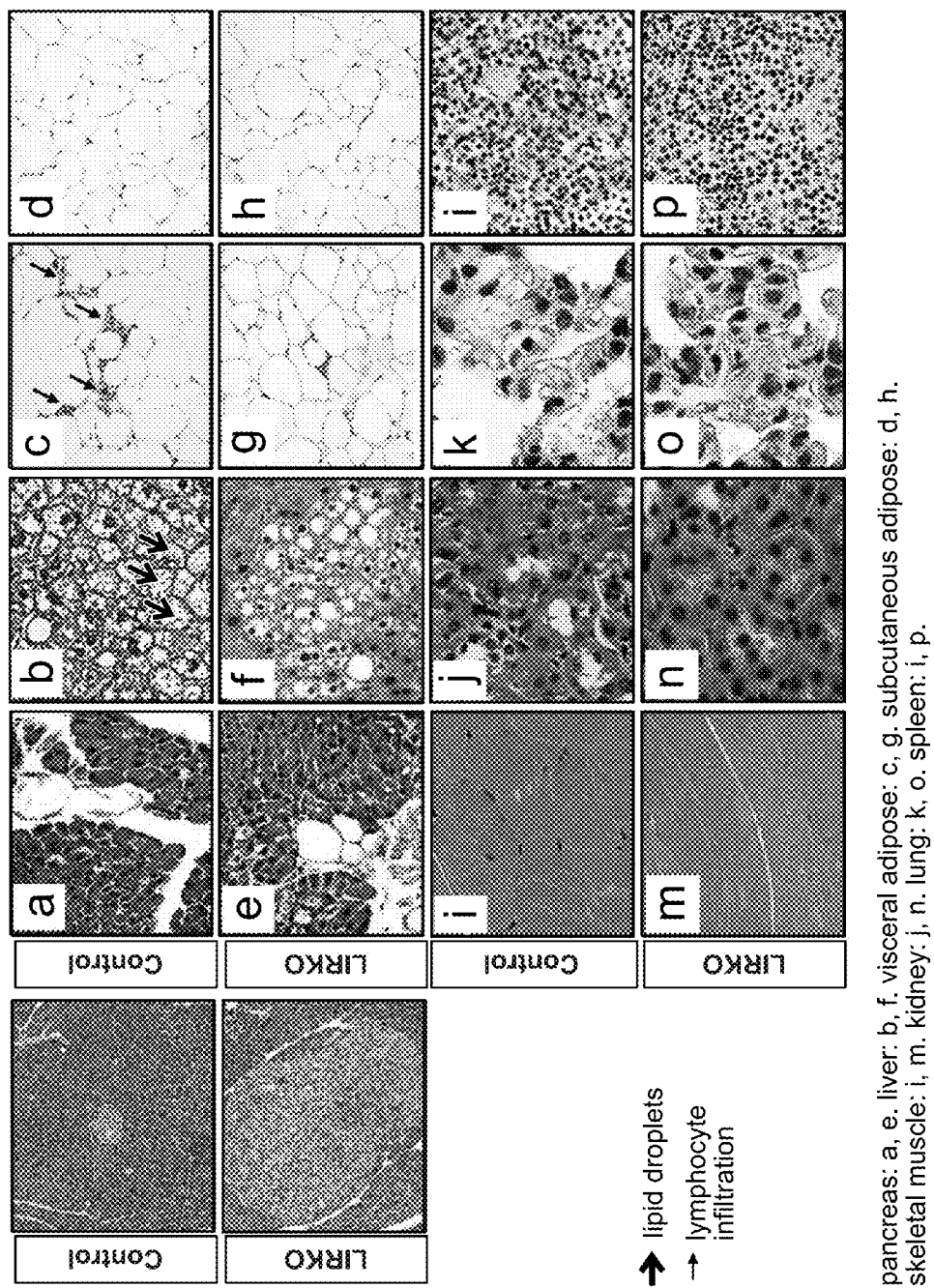
FIG. 6 shows hematoxylin and eosin staining of tissue sections from 12-month-old control and LIRKO mice. These data are related to data in FIG. 1 and Table 2. It represents an H & E based histological study of tissues from the LIRKO mouse.

Concerted efforts in diabetes research that were aimed at identifying molecules that specifically promote β cell regeneration without adverse proliferation of cells in other tissues. To determine whether Liver Insulin Receptor Knockout (LIRKO) mice, which manifest a dramatic hyperplasia of the endocrine pancreas, exhibit increased proliferation in extra-pancreatic tissues, we injected bromodeoxyuridine (BrdU; 100 mg/kg body weight) intraperitoneally in 3-month-old LIRKO mice and assessed proliferation of β cells, α cells, and cells in metabolic organs such as the liver, adipose and skeletal muscle, and in nonmetabolic tissues such as the lung, kidney, and spleen. We observed a 2-fold increase in β cell mass (LIRKO 1.32±0.2 versus control 0.68±0.08 mg; $p<0.05$; n=6) in LIRKO mice compared to littermate controls that was due to enhanced β cell proliferation evidenced by a 2.5-fold increase in BrdU incorporation (LIRKO 1%±0.08% versus control 0.4%±0.07% BrdU+β cells; $p<0.001$; n=6) and Ki67 staining (LIRKO 1.34%±0.1% versus control 0.51%±0.08% Ki67+β cells; $p<0.001$; n=6) in the LIRKOs. TUNEL staining did not reveal significant differences in the number of apoptotic β cells between groups. We also observed no difference in α cell proliferation (LIRKO 0.24%±0.09% versus control 0.29%±0.1% BrdU+ α cells; n=6) (FIGS. 1A-1F), or in the proliferation of cells in multiple non-β cell tissues, including visceral adipose, subcutaneous adipose, muscle, kidney, liver, or spleen. Although we did observe some increase in proliferating lung cells (LIRKO 0.7%±0.02% versus control 0.43%±0.08% BrdU+ cells; n=6; $p<0.05$) (FIGS. 1G and 1H), histological analyses of tissues dissected from 12-month-old LIRKOs revealed no tumor-like phenotypes (FIG. 6; Table 2), and the life span of the LIRKOs was similar to littermate controls. These data indicate that LIRKO mice exhibit a robust β cell-specific proliferation in response to insulin resistance.

TABLE 2

Histological characteristics of 12-month-old Control and LIRKO mice

|  | Control | LIRKO |
| --- | --- | --- |
| Pancreas | mild pancreatitis | very mild pancreatitis |
| Liver | severe steatosis | no steatosis + focal dysplasia + hyperplastic nodules |
| Skeletal muscle | normal | normal |
| Visceral adipose | severe lymphocyte infiltration | mild lymphocyte infiltration |
| Subcutaneous adipose | normal | normal |
| Spleen | normal | normal |
| Kidney | normal | normal |
| Lung | normal | normal |

Example 2

Circulating Nonneuronal Nonautonomous Factors Drive β Cell Replication in LIRKO Mice.

Figure 2:
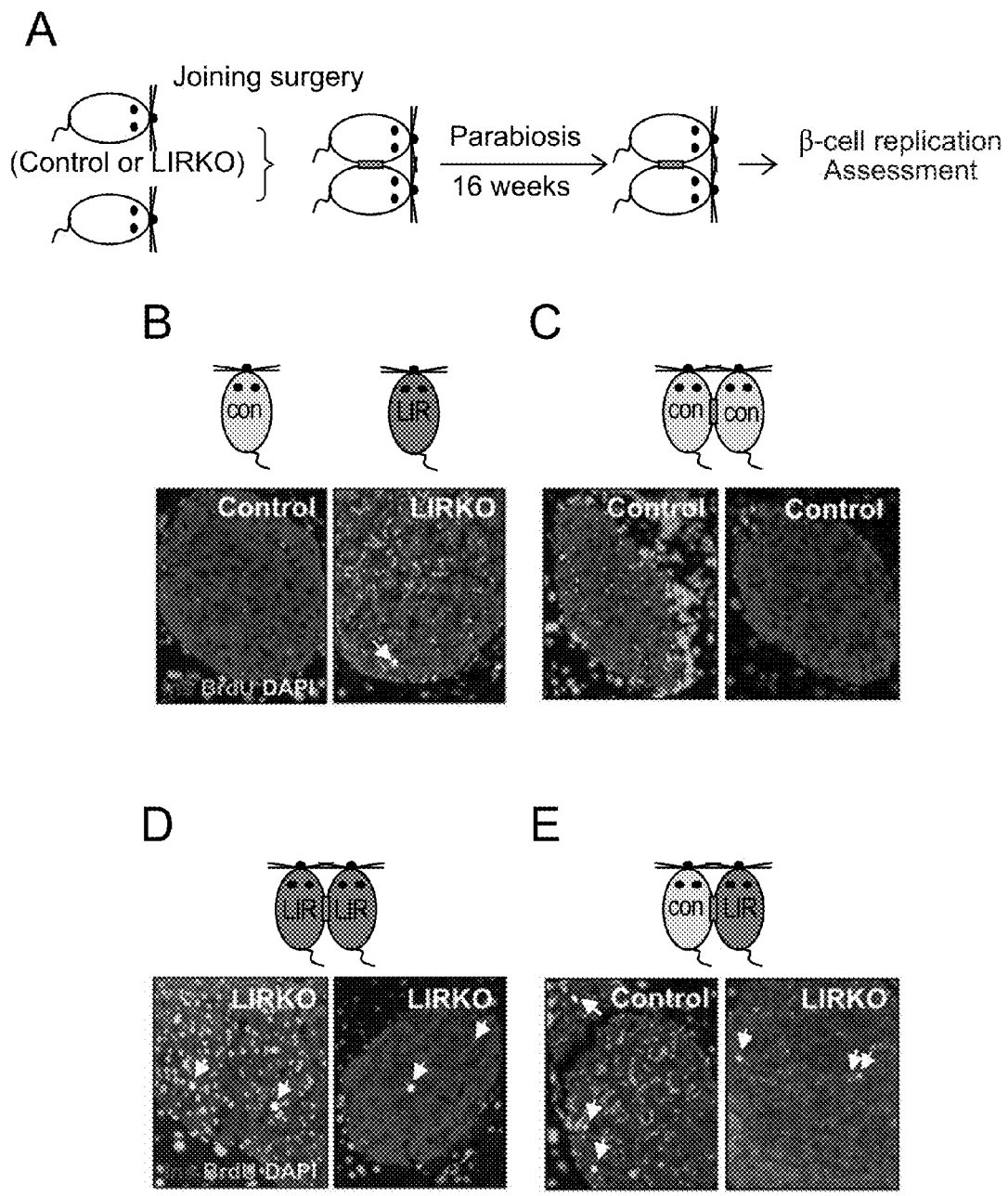
FIG. 2 (A-H) shows circulating nonneuronal nonautonomous factors drive β cell replication in the LIRKO mouse. (A) Schematic of the parabiosis experiment. See also, FIGS. 7, 8, and 9. (B-E) Single and parabiont models were intraperitoneally injected with BrdU (100 mg/kg body weight) 5 hr before animals were sacrificed, and pancreases were dissected and immunostained for insulin, BrdU, and DAPI. (F) Quantification of BrdU+ insulin+ cells: three sections separated by 80 mm were analyzed, and between 2,000 and 10,000 cells were counted in each group (n=5-6 in each parabionts group). (G) Schematic of the transplantation experiment. (H) Quantification of BrdU+ insulin+ cells in islet grafts as indicated: three to six islet graft sections were analyzed and counted between 2,000 and 10,000 cells in each group (n=3-5 in each group). Data represent mean±SEM. *p % 0.05.
Figure 7:
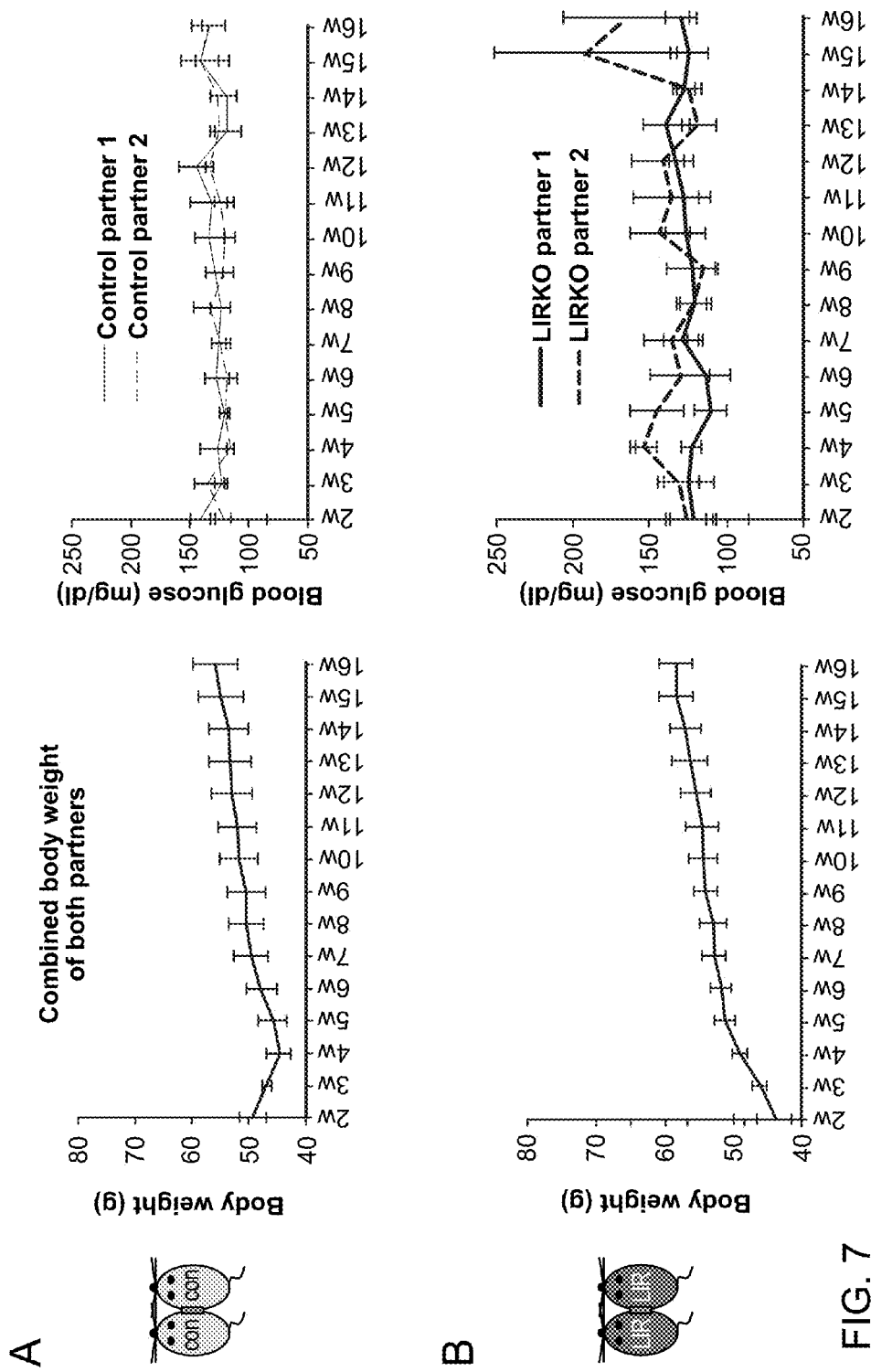
FIG. 7(A-C) shows weekly monitoring of body weight and blood glucose in parabionts. These data are related to data shown in FIG. 2A. The data indicates weight-gain in both groups of mice (A) con/con; (B) LIR/LIR and shows similar blood glucose levels in parabiont models (C) con/LIR over the 16-week period.
Figure 7:
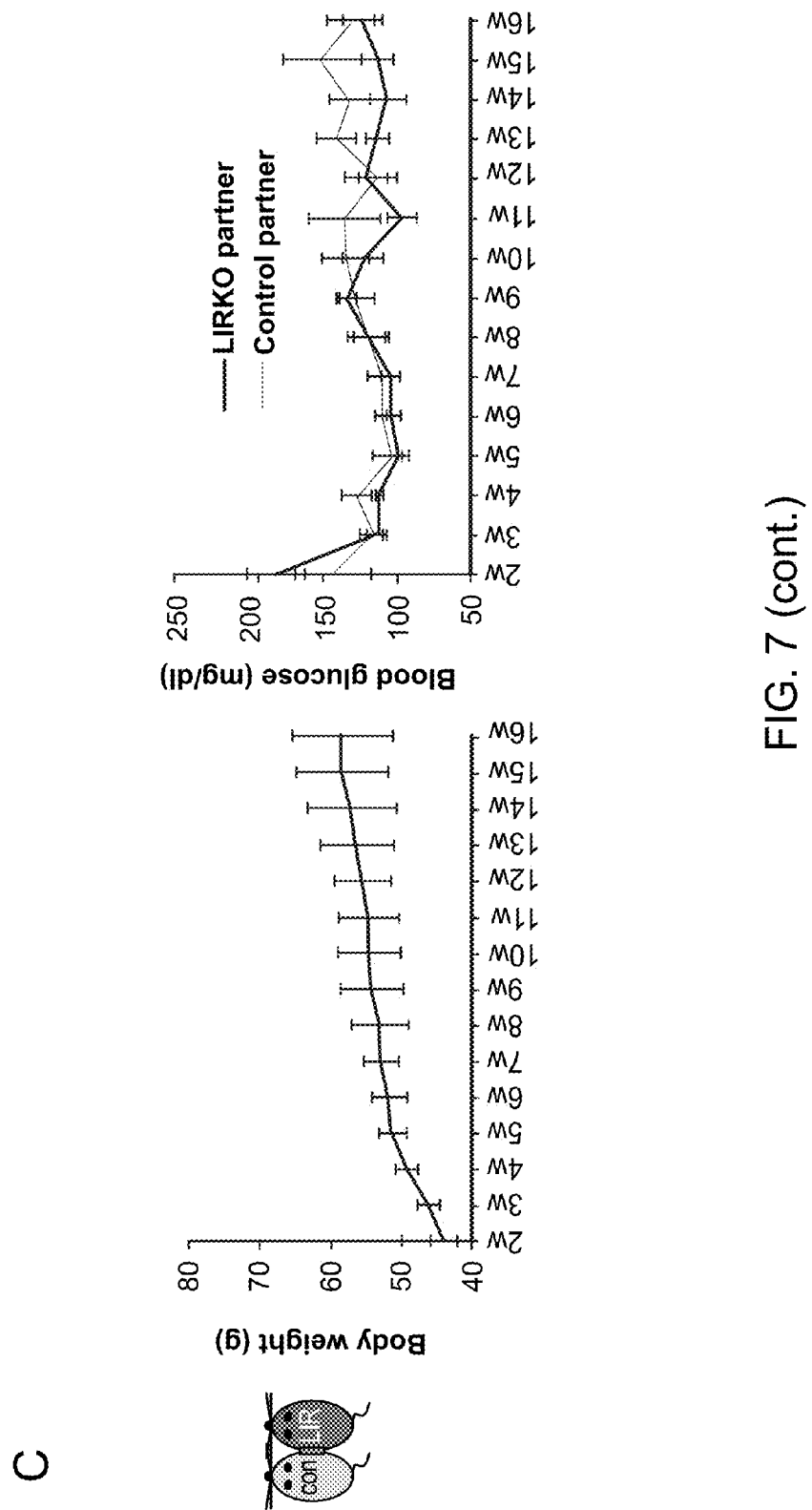
Figure 8:
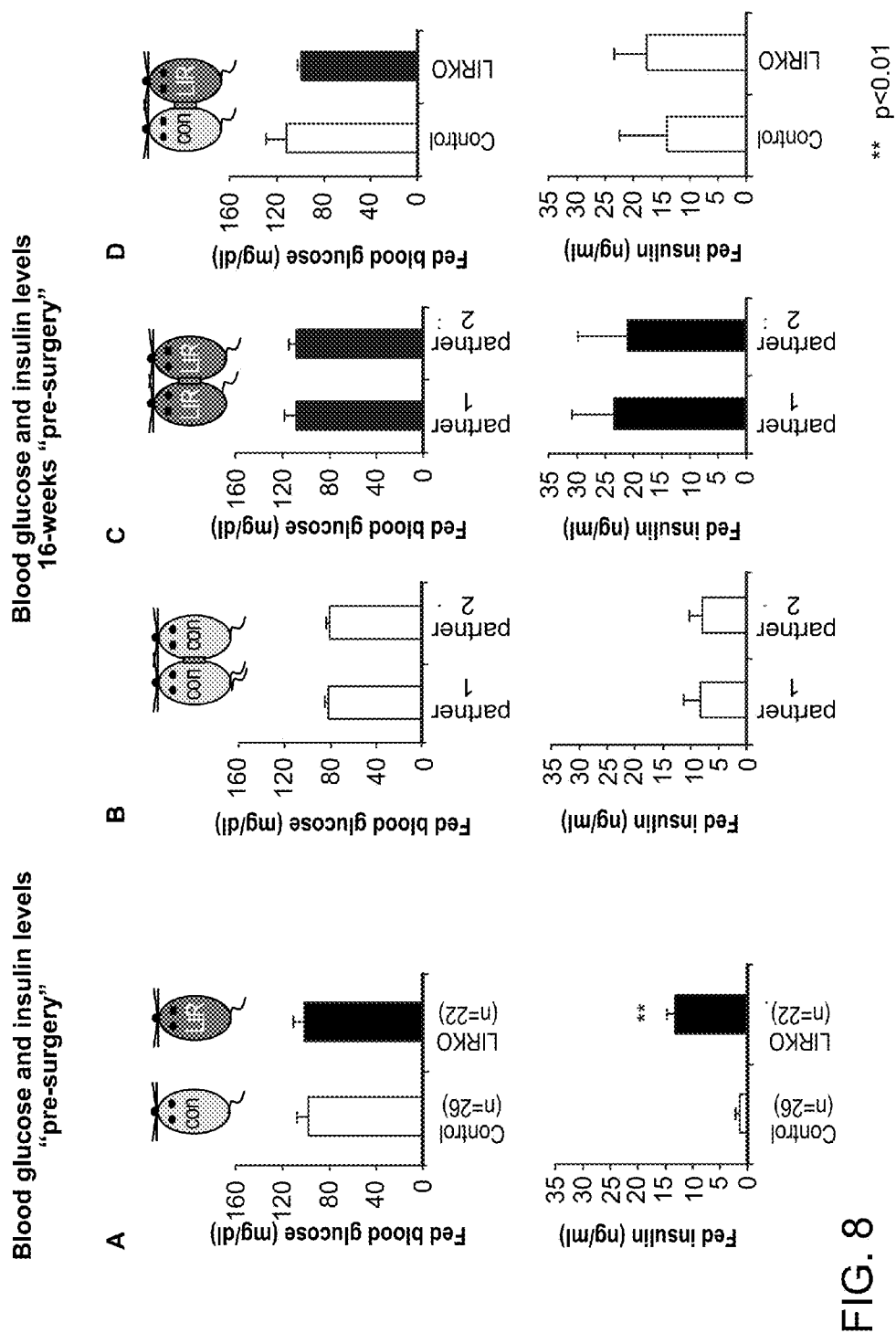
FIGS. 8(A & B) shows blood glucose and insulin assays in parabiont pairs pre-(A) con/LIR and postsurgery (B) con/con; (C) LIR/LIR; (D) con/LIR. These data are related to data shown in FIG. 2A. The data show glucose and insulin levels in parabiont models before and after a 16-week parabiosis period.

To directly address whether β cell proliferation in the LIRKO mouse is mediated by systemic factors, we first used a parabiosis model (Bunster, E., and Meyer, R. K. (1933). An improved method of parabiosis. Anat. Rec. 57, 339-43). Five to 6-week-old male mice were surgically joined at the shoulder and hip girdles, and successful anastomosis was confirmed within 2 weeks of joining by Evans Blue Dye injection (data not shown). Animals remained parabiosed for 16 weeks, and β cell replication was subsequently assessed by BrdU incorporation (FIG. 2A). Three surgical models were generated: control/control, control/LIRKO, and LIRKO/LIRKO. All parabiont groups grew normally, with a weekly increase in their body weights, and the blood glucose of the parabiont partners was within the normal range and did not significantly differ between groups (FIGS. 7A-7C).

Figure 9:
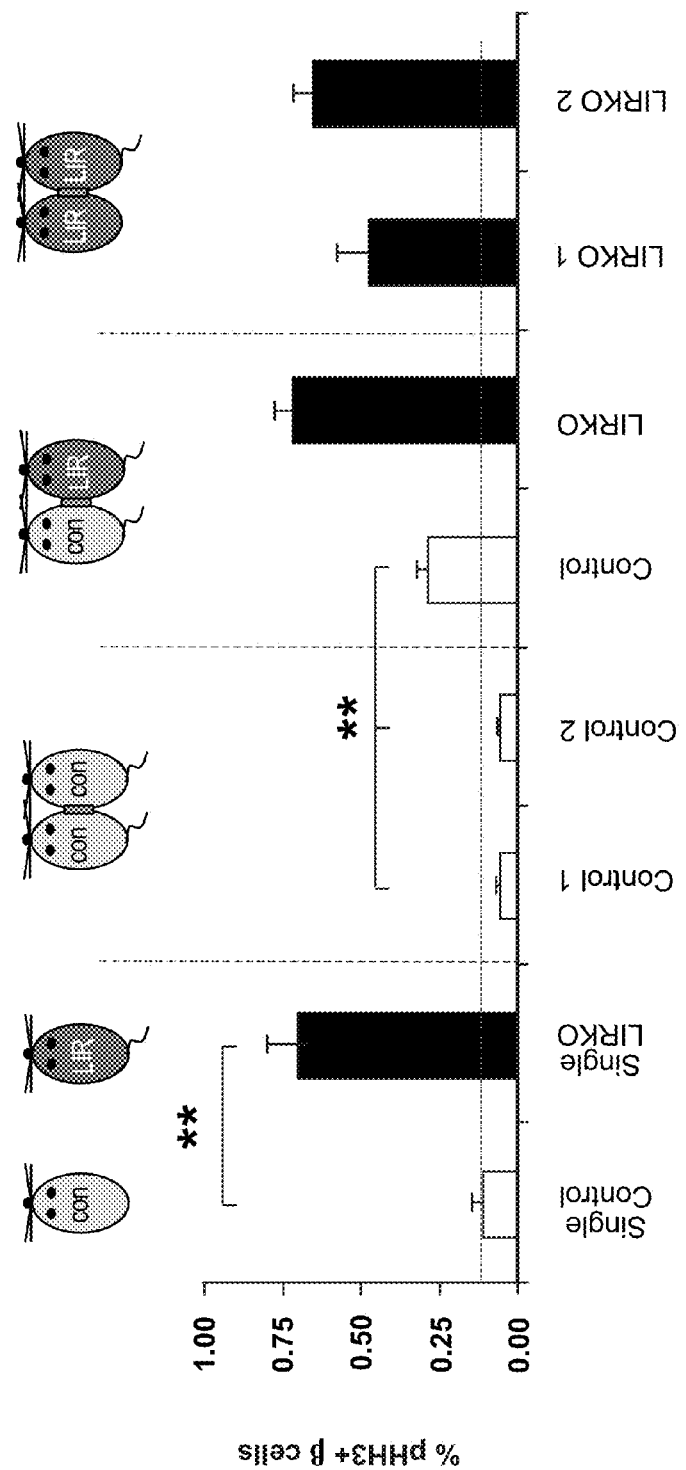
FIG. 9 shows quantification of pHH3+ insulin+ cells in parabiosis experiments. These data are related to data shown in FIG. 2A. These data support the observations regarding β cell proliferation in different parabiont models assessed by BrdU incorporation in FIG. 2A.

After 16 weeks of parabiosis, LIRKO and control parabionts displayed similar fasting blood glucose levels and circulating insulin levels and were higher in control partners joined with LIRKOs compared to nonparabiosed controls and controls parabiosed with controls (FIGS. 8A-8D). As expected, BrdU incorporation revealed low β cell mitosis in control mice and a significant elevation in LIRKO animals (control 0.03%±0.005% versus LIRKO 0.14%±0.02% BrdU+β cells; p<0.005; n=5-6). We also noted a low level of β cell proliferation in the control parabionts (FIGS. 2F and 9) compared to the single controls (FIGS. 1C and 1D). We believe this may be secondary to the parabiosis procedure itself and requires further investigation. BrdU incorporation was similar in pancreatic β cells of same-genotype parabionts: low in control/control (~0.03% BrdU+β cells; n=5-6); and high in LIRKO/LIRKO (~0.19% BrdU+β cells; n=5-6). Interestingly, BrdU incorporation was significantly increased in pancreatic β cells of control mice joined with LIRKO mice (control in control/LIRKO parabionts 0.09%±0.01% versus control in control/control parabionts [0.03%±0.004% and 0.03%±0.008%] BrdU+β cells; p<0.01; n=5-6) (FIGS. 2B-2F). The latter observations were confirmed by immunostaining for phospho-Histone H3 (pHH3) (FIG. 9). These data indicate the presence of cell nonautonomous, circulating factors produced in LIRKO mice that promote β cell replication. Previous studies have implicated neural pathways in modulating β cell proliferation in a cell-nonautonomous fashion (Imai, J., et al., (2008). Regulation of pancreatic beta cell mass by neuronal signals from the liver. Science 322, 1250-1254). To evaluate a possible influence of such neural effects on β cell proliferation in the LIRKO model, we undertook transplantation studies to assess β cell replication. A total of 125 size-matched islets freshly isolated from either control or LIRKO mice were transplanted under the kidney capsule of either control or LIRKO recipients. To minimize systematic error, each recipient mouse (control or LIRKO) was transplanted with two islet grafts, one derived from control and the other derived from LIRKO donors, under the left and right kidney, respectively (FIG. 2G). Sixteen weeks after transplantation, islet grafts were harvested, sectioned, and analyzed for β cell BrdU incorporation. As expected, control islets grafted into control animals exhibited minimal β cell proliferation (0.017%±0.017% BrdU+β cells). Intriguingly, the same donor-derived control islets showed an ~8-fold increase in β cell replication when transplanted instead into LIRKO recipients (0.139%±0.03% BrdU+β cells; p<0.05; n=3-5). Notably, LIRKO islets transplanted into LIRKO recipients exhibited robust β cell replication, reminiscent of the increased β cell proliferation seen in the pancreas of unmanipulated LIRKO mice, whereas this response was blunted when LIRKO islets were grafted instead into control animals (FIG. 2H). Taken together, these two complementary experimental strategies provide evidence that circulating nonneural and non-cell-autonomous factors contribute to expanding β cell mass in response to insulin resistance.

Example 3

LIRKO Serum Induces Selective β Cell Replication In Vivo.

Figure 3:
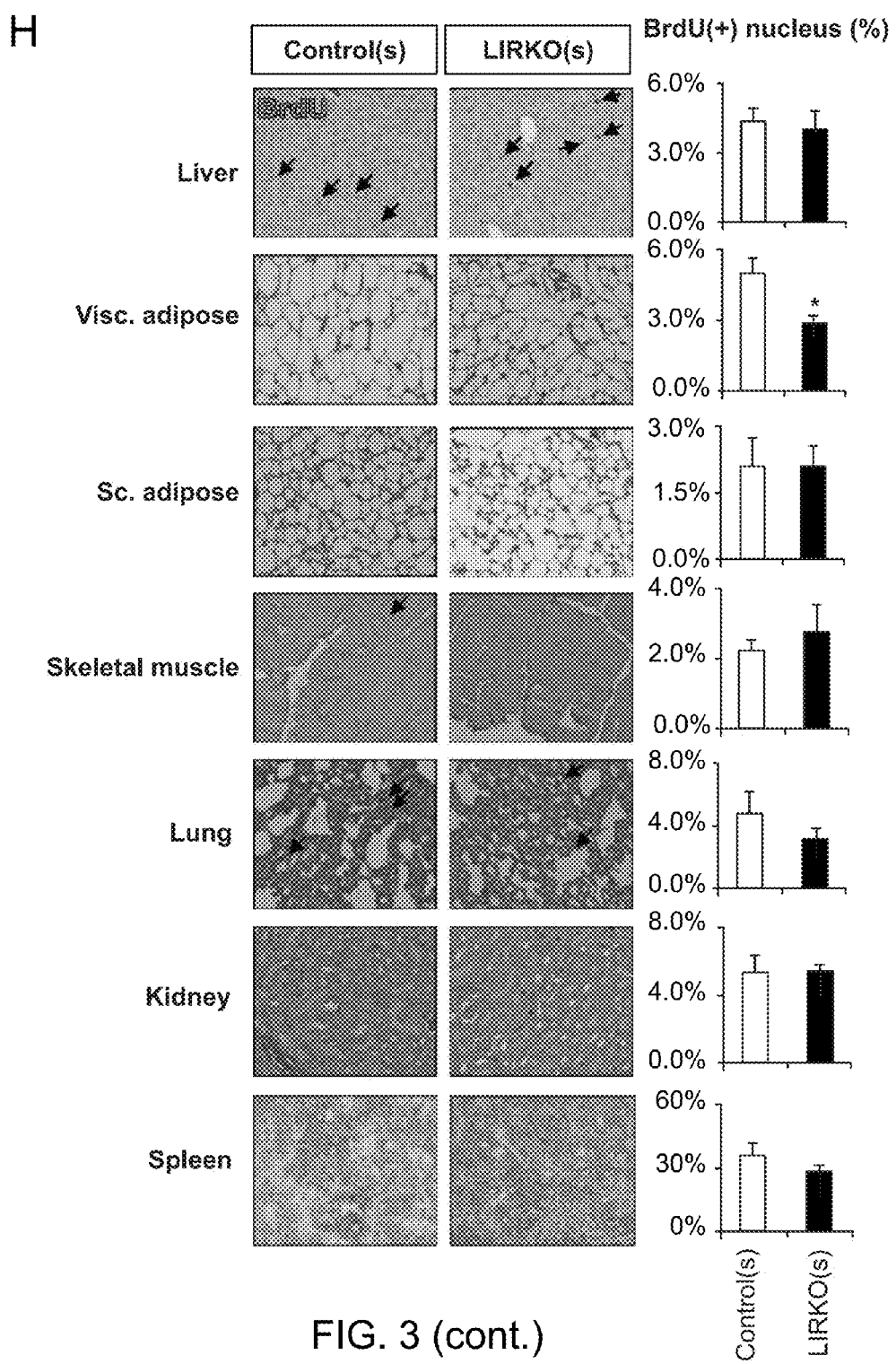
FIG. 3(A-H) shows LIRKO serum induces selective β cell replication in vivo. Five to 6-week-old mice were injected intraperitoneally twice daily with 150 ml serum derived from 6-month-old control or LIRKO mice on days 1, 3, and 5. BrdU was injected intraperitoneally (100 mg/kg body weight) on days 2, 4, and 6. Animals were sacrificed 5 hr before the last BrdU injection, and tissues were dissected for immunostaining studies. (A) Schematic of the experimental design. (B and C) Representative images and quantification of BrdU+ insulin+ cells: two sections separated by 80 mm were analyzed, and at least 4,000 insulin+ cells were counted for each animal. (D and E) Representative images and quantification of BrdU+ glucagon+ cells: 400-600 glucagon+ cells were counted in each animal. (F and G) Representative images and quantification of TUNEL+ insulin+ cells: at least 2,000 insulin+ cells were counted in each animal. (H) Representative images and quantification of nuclei BrdU+ in indicated tissues: for each animal, 4,000-5,000 cells were counted in sections from liver, kidney, spleen, and lung, and 1,500 cells were counted in sections from visceral (Visc.) and subcutaneous (Sc.) adipose tissue and skeletal muscle. Data represent mean±SEM. *p % 0.05 (n=3 in each group).

We next sought to evaluate the relative importance of bloodborne molecules versus cells in the induction of β cell proliferation in the LIRKO model. Five to 6-week-old male mice were injected intraperitoneally with freshly isolated serum from 6-month-old control or LIRKO mice, respectively, twice a day (150 ml per injection) on days 1, 3, and 5. The recipients were injected with BrdU (100 mg/kg body weight) once a day on days 2, 4, and 6. The pancreases were harvested on day 6 to assess b and a cell replication (FIG. 3A). Control mice injected with LIRKO serum (LIRKO(s)) displayed an ~2-fold increase in their endogenous β cell, but not a cell, replication compared to littermates injected with control serum (control(s)) (FIGS. 3B-3E). We saw no significant difference in the number of TUNEL+β cells (FIGS. 3F and 3G) between LIRKO(s) and control(s)-injected groups. Assessment of BrdU incorporation in extrapancreatic tissues, including liver, subcutaneous adipose, muscle, kidney, spleen, and lung, revealed no significant differences in proliferation between groups, whereas a mild decrease was observed in visceral adipose (FIG. 3H). This in vivo study confirms that a circulating molecule(s), stable in serum, selectively promotes β cell proliferation in the LIRKO model.

Example 4

LIRKO Serum Increases Mouse and Human Islet β Cell Replication In Vitro.

Figure 10:
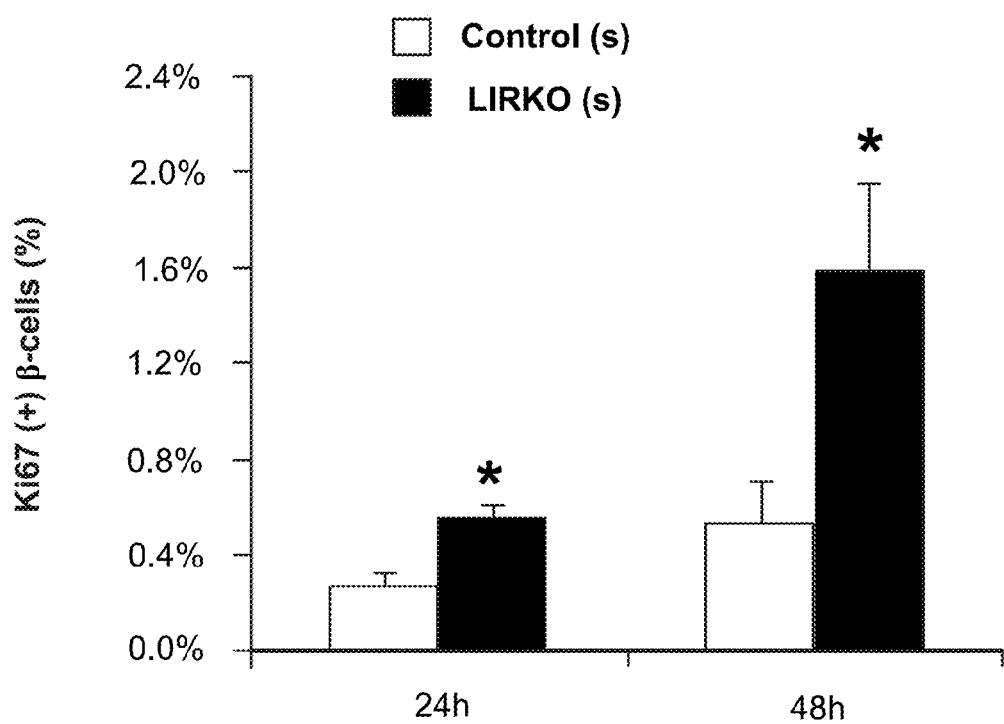
FIG. 10 shows quantification of Ki67+ insulin+ cells in serum-stimulated mouse islets. These data are related to data shown in FIG. 4A. The time course study presented in this figure is related to the serum stimulation experiments presented in FIG. 4A.

To gain further insight into the mode of action of this circulating β cell growth factor, we next established an in vitro functional assay to directly assess the impact of LIRKO or control serum on β cell replication in isolated mouse islets. We cultured islets in media containing serum from LIRKO or control mice and then assessed β cell proliferation using Ki67 immunostaining and fluorescence microscopy. Randomly selected Ki67+β cells in each of the groups in all experiments were confirmed by confocal microscopy (FIG. 4A). We first tested the ability of 6-month-old LIRKO serum to stimulate β cell proliferation and found that a 1:10 dilution of serum derived from LIRKO mice increased β cell proliferation in primary islets at 24 and 48 hr (FIG. 10). LIRKO serum from 3-month-old mice also enhanced β cell proliferation in mouse islets (LIRKO(s) 1.58%±0.3% versus control(s) 0.52%±0.1% Ki67+β cells; p<0.05; n=6). Moreover, mouse islets cultured in 12-month-old LIRKO serum showed a greater number of replicating β cells compared to islets incubated with age-matched control serum (LIRKO(s) 1.3%±0.5% versus control(s) 0.7%±0.2% Ki67+β cells; p=0.3; n=4-6) (FIGS. 4B and 4C); this increase lost its statistical significance probably due to an elevated insulin resistance in aging controls that itself contributed tops cell proliferation (Kulkarni, R. N., et al., (2003). Impact of genetic background on development of hyperinsulinemia and diabetes in insulin receptor/insulin receptor substrate-1 double heterozygous mice. Diabetes 52, 1528-1534; Mori, M. A., et al., (2010). A systems biology approach identifies inflammatory abnormalities between mouse strains prior to development of metabolic disease. Diabetes 59, 2960-2971). TUNEL staining showed no significant difference in β cell apoptosis in islets cultured in LIRKO(s) versus control(s) (FIG. 4D). Preliminary data indicate that the ability of the LIRKO serum to stimulate β cell proliferation is reduced when subjected to heat inactivation, suggesting that the putative circulating factor may be a protein (data not shown). To examine whether the proliferating effect of LIRKO serum is conserved across species, we next cultured human islets from nine healthy and two diabetic donors (for donor characteristics, see Table 3) in serum isolated from 12- to 18-month-old male LIRKO or control mice. Similar to the effects on mouse β cells, serum from LIRKO mice enhanced human islet β cell proliferation, albeit at a level lower than that reported in a recent study by Rieck, S., et al., (2012).

TABLE 3

Islet-donor characteristics

| Donor | Gender | Ethnicity/Race | Age (years) | BMI | Diabetic donor status | Experiment |
|---|---|---|---|---|---|---|
| 1 | Male | White | 55 | 20.1 | No | stimulation with serum |
| 2 | Male | White | 23 | 25.6 | No | stimulation with serum |
| 3 | Female | White | 18 | 26.4 | No | stimulation with serum |
| 4 | Male | Hispanic/Latino | 25 | 29.3 | No | stimulation with serum |
| 5 | Male | Hispanic/Latino | 50 | 26.5 | No | stimulation with serum |
| 6 | Unkown | Unkown | 64 | 30 | No | stimulation with serum |
| 7 | Female | African american | 41 | 42 | No | stimulation with serum |
| 8 | Male | White | 54 | 19.5 | No | stimulation with serum |
| 9 | Male | African american | 20 | 31.3 | No | stimulation with serum |
| 10 | Male | Unknown | 53 | 31 | T2D | stimulation with serum |
| 11 | Female | White | 38 | 37.8 | T2D on metformin | stimulation with serum |
| 12 | Unknown | Unknown | 65 | 31 | No | stimulation with LECM |
| 13 | Unknown | Unknown | 54 | 34 | T2D | stimulation with LECM |
| 14 | Male | White | 52 | 50 | T2D | stimulation with HCM |

Figure 4:
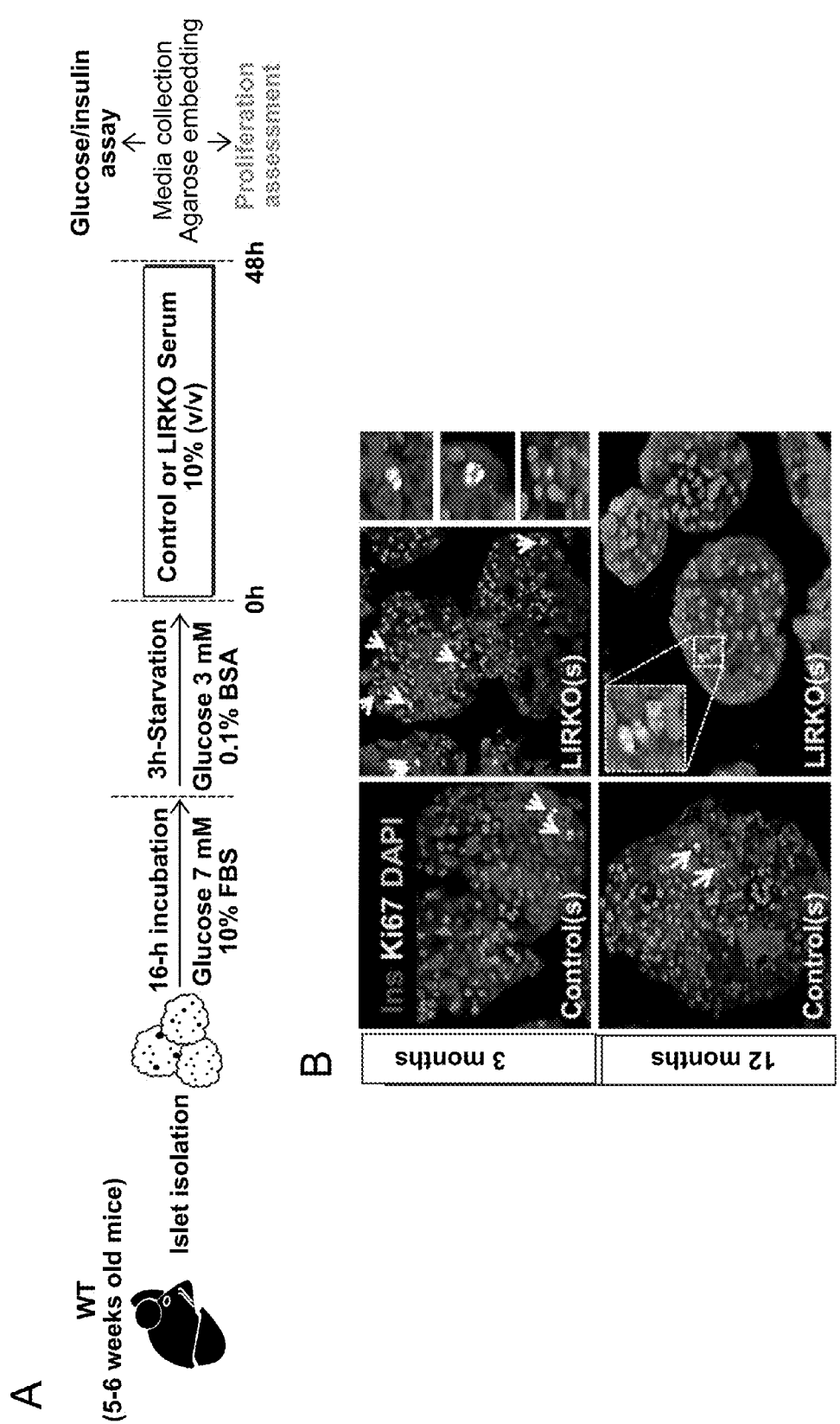
FIG. 4(A-F) shows LIRKO serum increases mouse and human Islet β cell replication in vitro. Five to 6-week-old mouse islets were stimulated with control or LIRKO serum for 48 hr. Islets were embedded in agarose and used for immunostaining studies. Culture media were assayed for glucose and insulin. WT: wild-type. (A) Schematic of the experimental protocol. See also FIGS. 10 and 11. (B) Representative images of mouse islets stimulated with sera derived from 3-month-old (upper panel) and 12-month-old animals (lower panel). (C) Quantification of Ki67+ insulin+ cells in (B): two sets of three serial sections separated by 80 mm were analyzed. At least 4,000-5,000 cells were counted in each experimental group (n=5 in each group). (D) Quantification of TUNEL+ insulin+ cells in (B): at least 3,000-4,000 cells were counted in each group (n=5 in each group). (E and F) Representative images of healthy and type 2 diabetic donor islets stimulated with control versus LIRKO serum for 24 hr. See also Table 3. (G) Quantification of Ki67+ insulin+cells in (E) and (F): three sets of three serial sections separated by 80 mm were analyzed. At least 3,000-4,000 cells were counted in each group. See also Table 3. Data represent mean±SEM. *p % 0.05. (See Serum Stimulation and Human Islet Studies sections in Experimental Procedures.).
Figure 4:
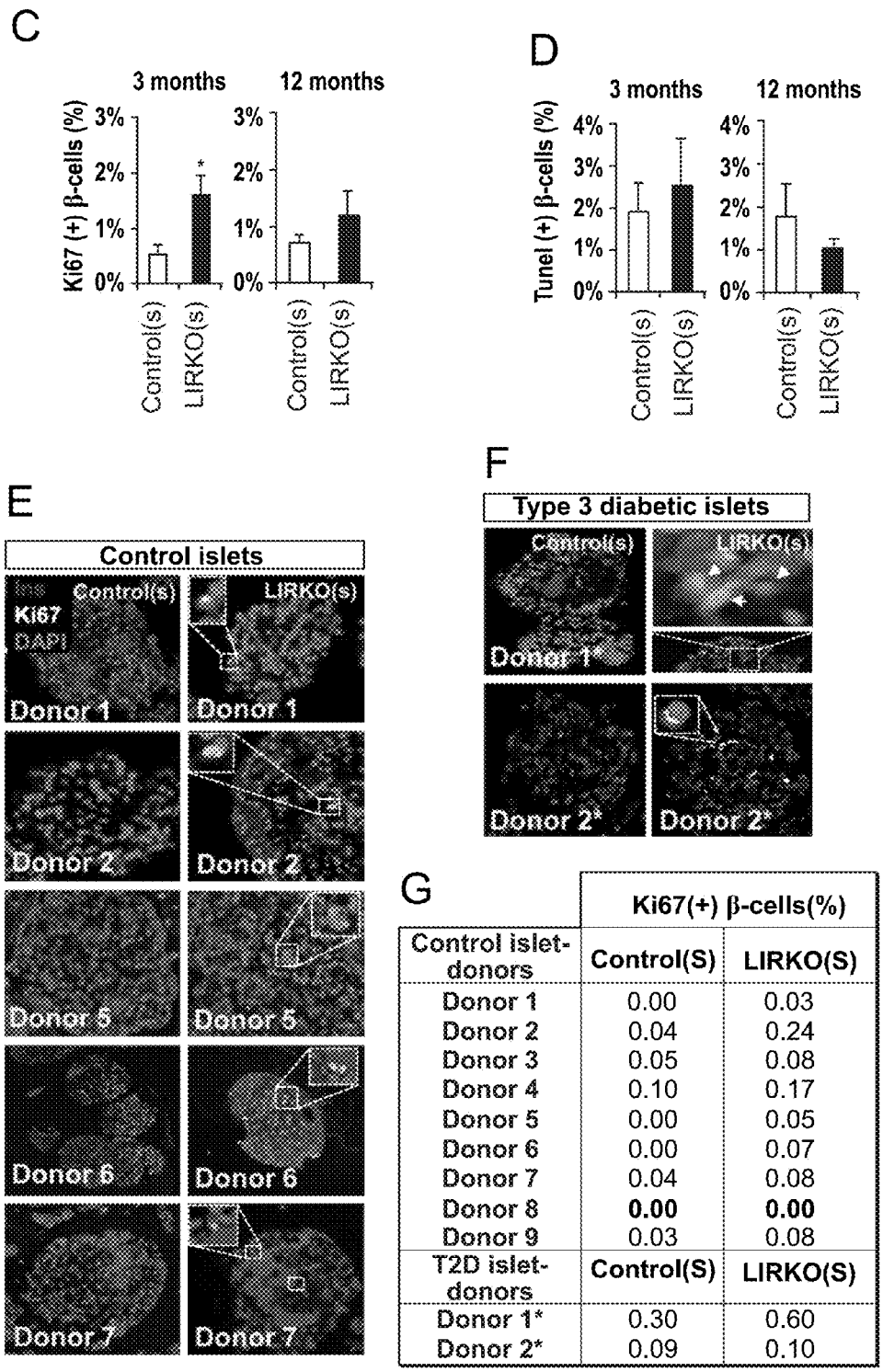
Figure 11:
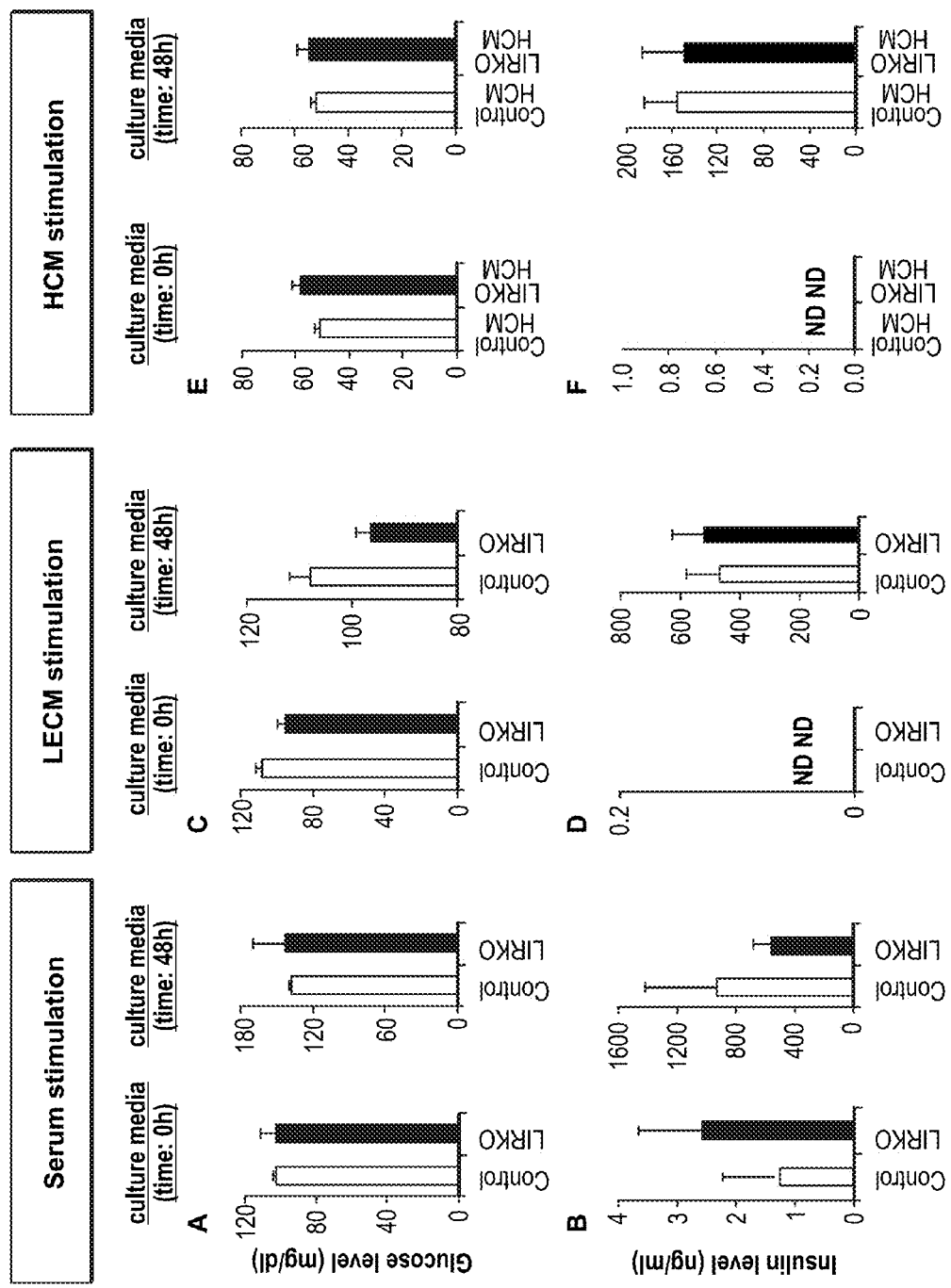
FIG. 11 (A-F) shows glucose (A, C and E) and insulin (B, D, F) assays in culture media. These data are related to data shown in FIGS. 4A and 5A. These data are related to in vitro islet culture experiments. They indicate the levels of glucose and insulin in the culture media before and after incubation of islets with serum (A, B) in FIG. 4A and with LECM (C, D) or HCM (E, F) in FIG. 5A.

Overexpression of hepatocyte nuclear factor-4a initiates cell cycle entry, but is not sufficient to promote b-cell expansion in human islets. Mol. Endocrinol. 26, 1590-1602). Importantly, LIRKO serum was also effective in promoting proliferation of islet β cells from patients with type 2 diabetes (FIGS. 4E-4G). Thus, the β cell mitogen(s) present in the circulation of LIRKO mice shows conserved activity toward mouse and human islets, including islets from patients with type 2 diabetes. Glucose and insulin have been reported to promote β cell growth (Assmann, A., et al., (2009). Growth factor control of pancreatic islet regeneration and function. Pediatr. Diabetes 10, 14-32; Assmann, A., et al., (2009b). Glucose effects on beta-cell growth and survival require activation of insulin receptors and insulin receptor substrate 2. Mol. Cell. Biol. 29, 3219-3228; Bonner-Weir, S., et al., (1989). Compensatory growth of pancreatic beta-cells in adult rats after short-term glucose infusion. Diabetes 38, 49-53) and are potential candidates in the LIRKO model, which manifests glucose intolerance and hyperinsulinemia (Michael, M. D., et al., (2000). Loss of insulin signaling in hepatocytes leads to severe insulin resistance and progressive hepatic dysfunction. Mol. Cell 6, 87-97). However, our observations suggest that glucose is not a dominant factor in the LIRKO mouse for several reasons. First, control mice parabiosed to LIRKOs for 16 weeks demonstrate up to a 7-fold increase in proliferation despite normal blood glucose levels (~120 mg/dl) during the parabiosis period (FIGS. 7A and 7C). Second, serum used to examine the effects on β cell proliferation (see FIG. 4A) was derived from either normoglycemic 3-month-old or hypoglycemic 12-month-old animals (data not shown). Finally, to further exclude a role for glucose, we cultured islets in a constant concentration of 5.5 mM glucose in experiments with serum from LIRKO or control mice (serum:culture media at 1:10 dilution) and observed an increase in proliferation in β cells only in the former group. Furthermore, the glucose levels in culture media at the beginning and at the end of islet incubation were similar in both groups (FIG. 11A). We believe that insulin may be permissive but unlikely to account for the high level of β cell proliferation in our model because the levels of insulin in the diluted serum (FIG. 11B) used in in vitro studies (see FIG. 4) are significantly lower compared to the levels found in the circulation in LIRKO mice (11.63±2.4 ng/ml [3-month-old LIRKOs] versus 2.59±1 ng/ml [diluted serum in culture media] and 17.8±4.4 ng/ml [12-month-old LIRKOs] versus 1.4±1.3 ng/ml [diluted serum in culture media]) (Table 1; Michael, M. D., et al., (2000). Loss of insulin signaling in hepatocytes leads to severe insulin resistance and progressive hepatic dysfunction. Mol. Cell 6, 87-97). Together, these data support the presence of a glucose- and insulin-independent liver-derived factor that promotes the expansion of β cell mass.

Example 5

Hepatocyte-Derived Factors Stimulate Mouse and Human Islet β Cell Replication In Vitro.

Figure 5:
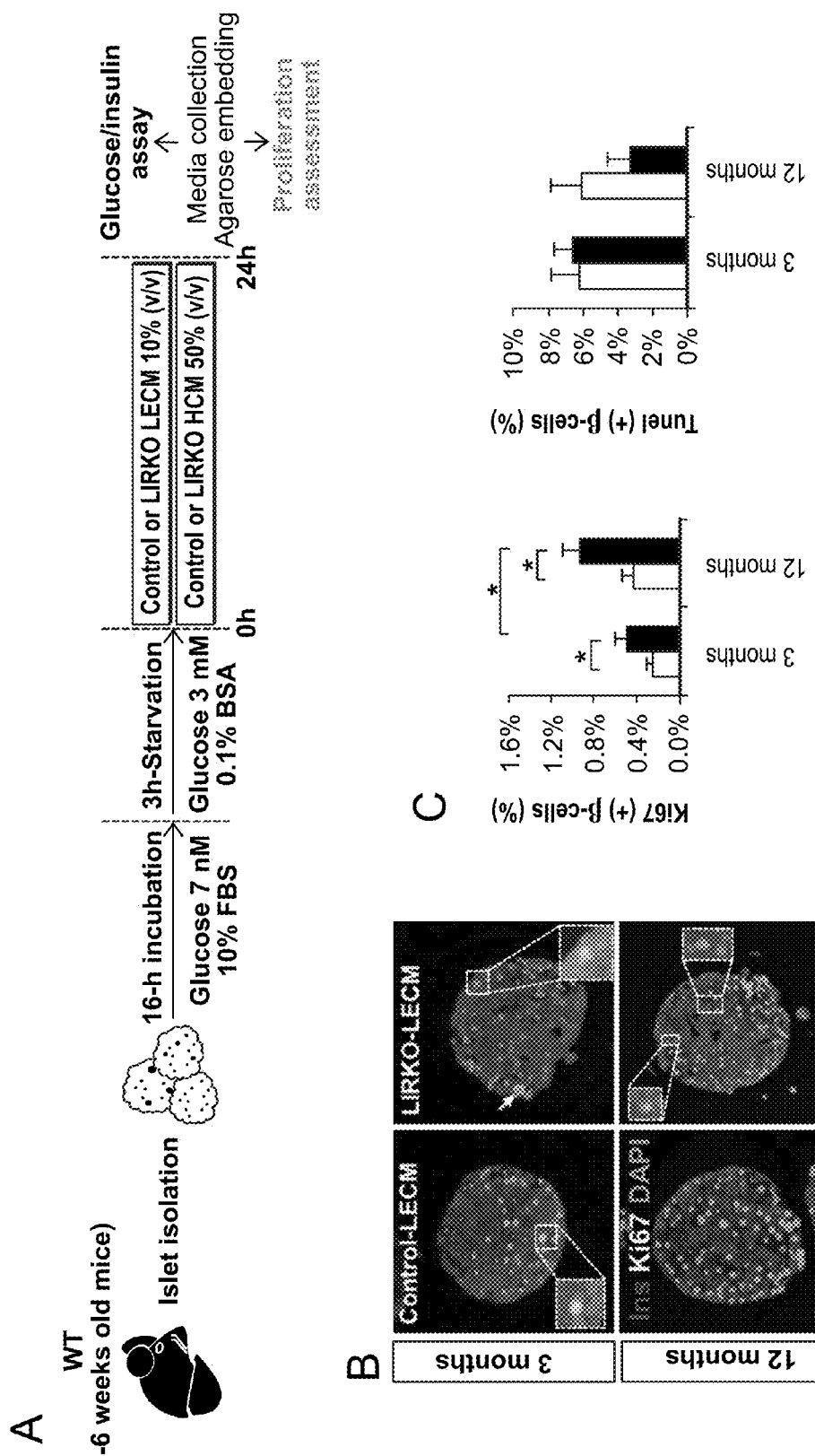
FIG. 5(A-I) shows hepatocyte-derived factors stimulate mouse and human Islet β cell replication in vitro. Five to 6-week-old mouse islets were stimulated for 24 hr with LECM or HCM obtained from control or LIRKO mice. Islets were embedded in agarose and subsequently analyzed by immunostaining. Culture media were assayed for glucose and insulin. (A) Schematic of the experimental protocol. See also FIG. 11. (B) Representative images of mouse islets stimulated with LECM derived from 3-month-old (upper panel) and 12-month-old animals (lower panel). (C) Quantification of Ki67+ insulin+ cells (upper panel) and TUNEL+ insulin+ cells (lower panel): at least 3,000-5,000 cells were counted in each experimental group (n=5 in each group). (D) Representative images of healthy human donor islets (upper panel) and type 2 diabetic donor islets (lower panel) treated for 24 hr with LECM derived from control versus LIRKO mice. See also Table 3. (E) Quantification of Ki67+ insulin+ cells in (D): between 3,000 and 4,000 cells were counted in each condition (Control LECM versus LIRKO LECM) in control islets, and at least 2,000 cells were counted in each experimental group for type 2 diabetic islets. See also Table 3. (F) Representative images of mouse islets stimulated with HCM derived from 6-month-old control versus LIRKO mice or fibroblast-conditioned media (FCM). (G) Quantification of Ki67+ insulin+ cells (upper panel) and TUNEL+ insulin+ cells (lower panel): between 4,000 and 5,000 cells were counted in each experimental group (Control HCM versus LIRKO HCM) (n=5 in each group). (H) Representative images of type 2 diabetic donor islets stimulated with control or LIRKO HCM. See also Table 3. (I) Quantification of Ki67+ insulin+ cells in (H): at least 2,000 cells were counted in each experimental condition. See also Table 3. Data represent mean±SEM. *p % 0.05. (See LECM Stimulation, HCM Stimulation, and Human Islet Studies sections in Experimental Procedures.)
Figure 5:
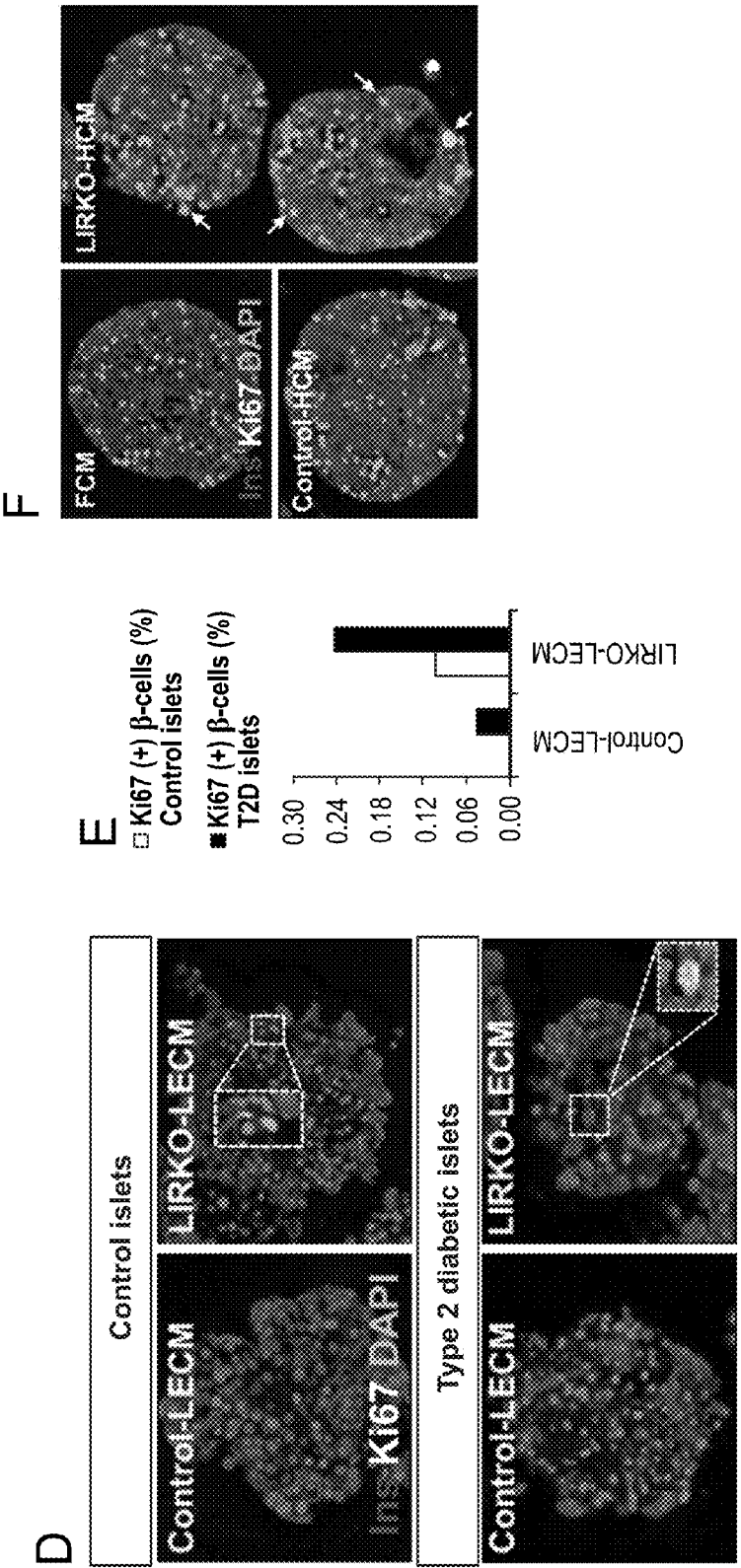
Figure 5:
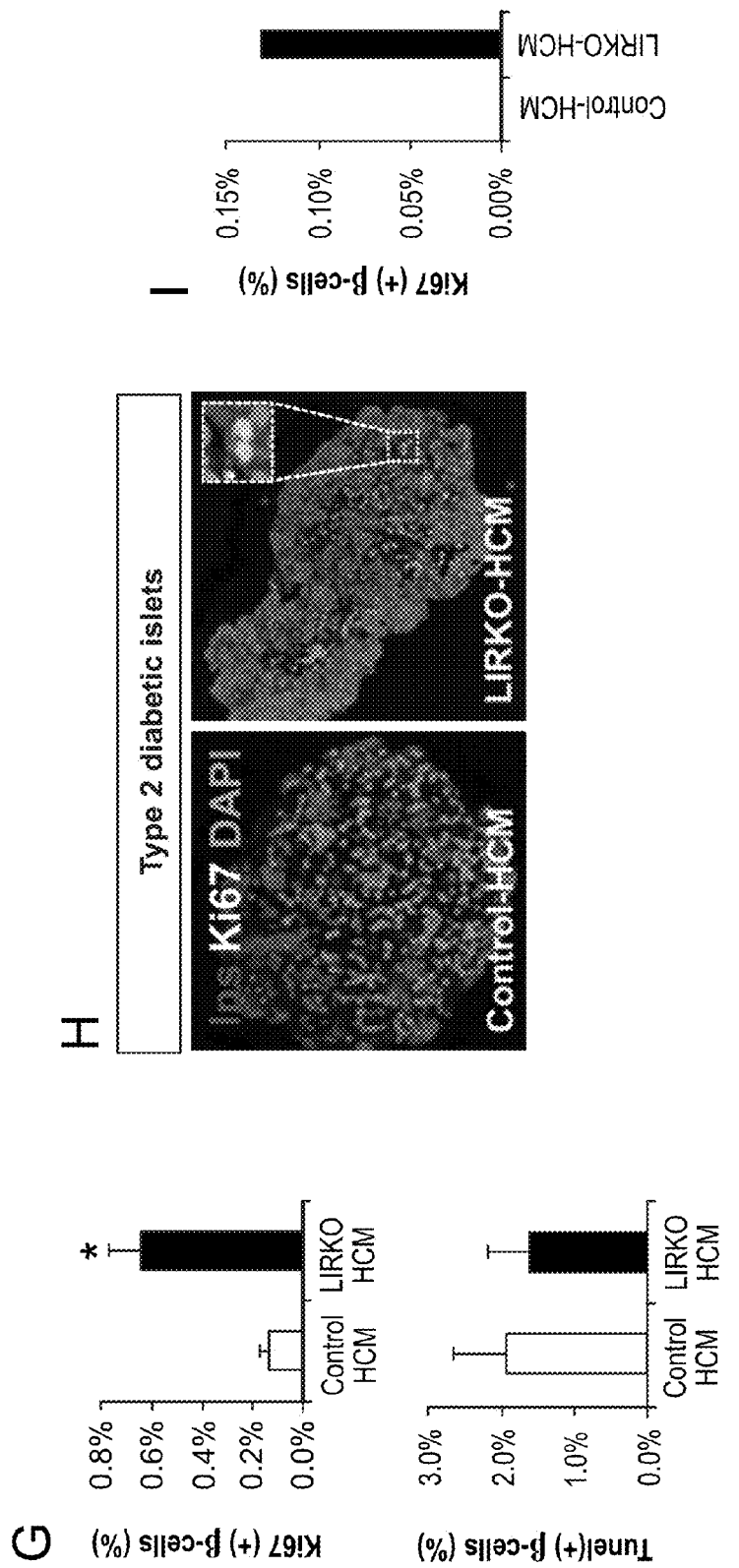

The common embryonic origin of the liver and the pancreas (Zaret, K. S. (2008). Genetic programming of liver and pancreas progenitors: lessons for stem-cell differentiation. Nat. Rev. Genet. 9, 329-340) coupled with the robust β cell proliferation response to tissue-specific insulin resistance in the liver compared to the virtual lack of a compensatory response when insulin resistance was restricted to muscle (Bruning, J. C., et al., (1998). A muscle-specific insulin receptor knockout exhibits features of the metabolic syndrome of NIDDM without altering glucose tolerance. Mol. Cell 2, 559-569), adipose (Blüher, M., et al., (2002). Adipose tissue selective insulin receptor knockout protects against obesity and obesity-related glucose intolerance. Dev. Cell 3, 25-38), or brain (Bruning, J. C., et al., (2000). Role of brain insulin receptor in control of body weight and reproduction. Science 289, 2122-2125) prompted us to hypothesize that the liver serves as a source of β cell growth factor(s) in response to metabolic insults such as insulin resistance. To test this hypothesis, we collected conditioned media from liver explant cultures (LECM) from either 3- or 12-monthold LIRKO or control animals and evaluated their effects on β cell proliferation in mouse islets (FIG. 5A). Ki67-positive β cells were significantly elevated in islets cultured in LECM from either 3- or 12-month-old LIRKO mice, compared to cells cultured in LECM derived from age-matched controls (FIG. 5B). Interestingly, whereas mouse islets cultured in control LECM derived from 3- and 12-month-old animals displayed similar levels of proliferation, the levels were 2-fold higher in cultures containing 12-month-old LIRKO-LECM compared to 3-month-old control LECM (FIG. 5C). This age-dependent effect of LIRKO-LECM is consistent with the age-dependent increase in β cell proliferation in LIRKO mice (Okada, T., et al., (2007). Insulin receptors in beta-cells are critical for islet compensatory growth response to insulin resistance. Proc. Natl. Acad. Sci. USA 104, 8977-8982). Similarly, β cells in islets obtained from healthy human controls and patients with type 2 diabetes (for donor characteristics, see Table 3) cultured in LECM derived from LIRKO animals exhibited increased proliferation compared to islets from the same donors cultured in control LECM (FIGS. 5D and 5E). The liver contains multiple cell types, including hepatocytes, Kupffer cells, and endothelial cells (Si-Tayeb, K., et al. (2010). Organogenesis and development of the liver. Dev. Cell 18, 175-189). To determine whether the growth factor activity in LIRKO serum is a product of hepatocytes or nonhepatic cells, we used conditioned media from cultures of primary hepatocytes (HCM), isolated from control or LIRKO mice in an in vitro β cell proliferation assay. Primary mouse islets cultured in LIRKO HCM exhibited markedly increased β cell proliferation compared to islets stimulated with control HCM (control HCM, 0.13%±0.03% versus LIRKO HCM, 0.64%±0.12%; p<0.05; n=5). The number of TUNEL+β cells was similar in both conditions (FIGS. 5F and 5G). Furthermore, the proliferative effect of LIRKO HCM was also evident when human islets obtained from a patient with type 2 diabetes (for donor characteristics, see Table 3) were exposed to LIRKO HCM compared to control HCM (FIGS. 5H and 5I). Thus, insulin-resistant hepatocytes produce a β cell growth-promoting factor(s) that enhances proliferation of mouse and human β cells. Although numerous signaling pathways impacting β cell growth have been documented (Kulkarni, R. N., et al., (2012). Human β-cell proliferation and intracellular signaling: driving in the dark without a road map. Diabetes 61, 2205-2213), specific blood-borne molecules that trigger β cell replication directly in response to insulin resistance have, to our knowledge, not been reported. The absence of a consistent increase in one or more growth factors in the serum of the LIRKOs (Table 1) supports the notion that additional unidentified factors are necessary to promote the full magnitude of proliferation observed in the LIRKO model. In summary, we provide evidence that a conserved systemic hepatocyte-derived growth factor(s) promotes β cell proliferation in mouse and human islets, supporting a liver-to-pancreas axis in the adaptive β cell growth response to insulin resistance.

Example 6

A Role for SerpinB1 and Related Family Members on Mouse and Human β-Cell Proliferation.

Pancreatic β-cell dysfunction underlies the development of both type1 and type 2 diabetes. Although the natural history of both forms diabetes is different, reduced functional β-cell mass is a common hallmark in both diseases. Regenerative approaches represent an attractive strategy to increase the number of functional β-cells. In this context, we recently reported (El Ouaamari, et al, *Cell Reports,* 2013, 3:1-10) the existence possible of liver-derived systemic factors capable of stimulating β-cell proliferation in Liver Insulin Receptor Knockout mouse (LIRKO), a unique model of islet hyperplasia and increased β-cell mass caused by insulin resistance.

Using comprehensive Affymetrix and Proteomics approaches we have now identified the superfamily of Serpin proteins as factors of β-cell growth. Among the family members, SerpinB1 was identified as the being a consistently up-regulated hepatocyte-derived systemic β-cell trophic factor.

Identification of SERPINB1 as a new potential beta cell growth factor from LIRKO mouse—Method: Proteomic analysis of hepatocyte conditioned media.
Pre-Enrichment on Nanozeolites Nanozeolite LTL nanoparticles were obtained from NanoScape AG, Germany. Adsorption of proteins on the surface of Nanozeolite LTL was carried out for 90 min at 4° C. by incubation of proteins from hepatocyte conditioned media (0.1 mg/ml) and nanoparticles (0.1 mg/ml) in suspension in PBS. After centrifugal separation at 16000 g during 20 min, proteins bound to nanoparticles are washed twice in 0.1M ammonium carbonate buffer, ph 8.0.

Protein samples were resolved by SDS-PAGE on NuPAGE® Novex® 4-12% Bis-Tris gels using the NuPAGE® MES SDS Running Buffer according to the manufacturer's instructions (Invitrogen, Grand Island, N.Y.) stained using the SilverQuest™ silver staining kit from Invitrogen.
Proteolytic Digestion The proteins captured on nanozeolites were reduced in the presence of 10 mM dithiothreitol, 0.05% AALS (Anionic Acid Labile Surfactants from Protea Biosciences) in 50 mM ammonium carbonate buffer, pH 8.0 at 56° C. for 30 min and then alkylated by adding 20 mM iodoacetamide for 30 min at room temperature in the dark.

After the reduction and alkylation steps, bound proteins were digested with LysC (1/50 w/w), 4 hrs at 37° C. and then with trypsin (1/50 w/w) for 18 hr at 37° C.

After centrifugation, protein digests were collected, and AALS hydrolyzed with 1% TFA at 37° C. min. Finally enzymatic digests were subjected to MS analysis.
LC-MS Analysis LC-MS (Liquid Chromatograph Mass Spectrometer) experiments were performed on NanoAcquity UPLC (Waters, Milford, Mass.) connected to a hybrid LTQ (Linear Trap Quadropole) Orbitrap Velos™ mass spectrometer (Thermo Fisher Scientific, Waltham, Mass.) equipped with a nanoelectrospray source. Protein digests were loaded onto a nanoAcquity UPLC Trap column (Symmetry C18, 5 µm, 180 µm×20 mm, Waters) and washed with 0.2% formic acid at 20 µL/min for 5 min. Peptides were then eluted on a C18 reverse-phase nanoAcquity column (BEH130 C18, 1.7 µm, 75 µm×250 mm, Waters) with a linear gradient of 7-30% solvent B ($H_2O/CH_3CN/HCOOH$, 10:90:0.2, by vol.) for 120 min, 30-90% solvent B for 20 min, and 90% solvent B for 5 min, at a flow rate of 250 nL/min.

The mass spectrometer was operated in the data-dependent mode to automatically switch between MS and MS/MS acquisition. Survey full scan MS spectra (from m/z 300-1700) were acquired in the Orbitrap with a resolution of 60,000 at m/z: 400. The AGC (automated gain control) was set to $1\times10^6$ with a maximum injection time of 500 ms. The most intense ions (up to 20) were then isolated for fragmentation in the LTQ linear ion trap using a normalized collision energy of 28% at the default activation q of 0.25 with an AGC settings of $2\times10^4$ and a maximum injection time of 200 ms. The dynamic exclusion time window was set to 150 s. Samples were injected in triplicate.
LC-MS/MS Data Processing LC-MS/MS data, acquired using the Xcalibur software (version 2.07, Thermo-Fisher Scientific), were processed using a Visual Basic program software developed using XRawfile libraries (distributed by Thermo-Fisher Scientific) . Similar programs are known to and can be developed by one of ordinary skill in the art. Three different files were generated by this program: the first one corresponds to a MS/MS peak list (MGF file) which will be used for database searching. This MGF file contains the exact parent mass and the retention time (RT) associated with each LTQ-MS/MS spectrum. The exact parent mass is the $^{12}C$ isotope ion mass of the most intense isotopic pattern detected on the high resolution Orbitrap MS parallel scan and included in the LTQ-MS/MS selection window. The RT is issued from the LTQ-MS/MS scan. The second file is a MS/MS log file which reports, for each acquired MS/MS, the scan number, the $^{12}C$ isotope exact mass, the RT and the parent filter (LTQ selection window). The third file corresponds to the conversion of the high resolution MS raw data file into a "csv" format file which will be used for quantitative analysis.

Database Searching

Database searches were done using our internal MASCOT server (version 2.1, matrix Science; http://www.matrixscience.com/) using the Swiss-Prot human database containing 402,482 entries. The search parameters used for post-translational modifications were a fixed modification of +57.02146 Da on cysteine residues (carboxyamidomethylation) and dynamic modifications of +15.99491 on methionine residues (oxidation), of +42.010565 on protein N-terminal residues (N-terminal acetylation) and −17.026549 on N-terminal glutamine residues (N-Pyroglu). The precursor mass tolerance was set to 5 ppm and the fragment ion tolerance was set to 0.5 Da. The number of missed cleavage sites for trypsin was set to 2. Mascot result files (".dat" files) were imported into Scaffold software (www.proteomesoftware.com/). Queries were also used for XTandem parallel Database Search. The compiled results of both database searches were exported.

Quantitative Analysis and Statistical Analysis

Quantitative differential analysis of proteins was realized using a label free analysis with an in-house DIFFTAL (DIFferential Fourier Transform Analysis) software algorithm. DIFFTAL Algorithm Overview. DIFFTAL is a set of software tools developed in Sanofi under MatLab environment (www.mathworks.com) for label-free differential analysis of complex proteomic mixtures dedicated to data recorded with high resolution MSMS instruments.

DIFFTAL runs in 6 main steps. These steps consist of the following: (1) Feature detection, (2) MS matching, (3) MS/MS annotations, (4) MS/MS matching, (5) Peptide quantification report and (6) Protein relative quantifications.

Step 1: Feature detection. Each LC/MS file is treated independently for feature detection. The signal apparition is detected scan by scan by analyzing the evolution of the average signal of 3 consecutive scans. Feature detection is achieved using the peptide isotopic patterns calculated with "Averagine" algorithm. At the end of the process, a matrix of the features detected in the 3D space (m/z (mass/charge), RT (retention time) and intensity) is stored. This matrix contains links to retrieve the corresponding processed signals, which are stored in a temporary data bank.

Step 2: MS matching. All LC-MS data are matched together using a progressive alignment procedure. First, the most intense detected features are matched in agreement with m/z and RT precision windows defined by the user. Then, all peptides are used to compute a specific RT alignment model. A definitive RT window is calculated according to the dispersion observed between real and calculated RTs. Finally, every remaining unmatched m/z is checked by going back to the processed signal stored during the feature detection step. This last point allows a very confident determination of the unmatched feature class.

Step 3: MS/MS annotations. This step corresponds to the data bank search previously reported in the "Database Searching" paragraph.

Step 4: MS/MS matching. MSMS Spectrum reports exported from Scaffold are matched with the matrix of detected features using the corresponding acquisition MS/MS log files (see LC-MS/MS data processing). This matching requires starting and ending time points of each feature. Indeed, the RT feature is the time at the maximum intensity of the observed MS signal, whereas the MS/MS spectrum is recorded at any time during the peptide elution. In case of ambiguity, the comparison between the exact isotopic profile calculated from the MS/MS sequence and the detected signal at the feature RT is used for sorting. Another routine has been also introduced in the software that quantifies only the MS/MS identified peptides according to the following scheme: the time profiles of the 2 major isotopes of each identified peptide are computed in a small time window where the MS/MS spectrum was recorded. Only the co-eluted signals of these 2 isotopes are analyzed to determine the peptide RT. The 3 scans averaged signal centered at this time is then compared with the full theoretical peptide isotopic pattern. This additional quantification is compared to the first one to generate a final result report. The convergence of these two quantification routines is used to improve the quantification confidence and identification coverage.

Step 5: Peptide Quantification report: Peptide quantification is calculated from the statistical analysis of the previous matrix. Statistical analyses were realized with DanteR program, an R based software written by Tom Taverner (Thomas.Taverner@pnl.gov and Ashoka Polpitiya for the U.S. Department of Energy (PNNL, Richland, Wash., USA: on the world wide web (www): omics.pnl.gov/software). The median intensity value of the detected feature population is used to normalize the 3 replicate injections of the same sample. Only peptides detected at least 2 times (over replicates) are kept and an average intensity value per sample is calculated for each peptide. A threshold value representing the minimum detectable signal level is used instead of quantification for non detected peptide.

As non detected peptide intensities are replaced by detection threshold, a protein which is identified, for example, in the treated sample but not detected in the control sample is represented with a minimum positive fold change which is the result of the treated signal divided by the minimum detectable signal.

Step 6: Protein quantification: Finally, peptides arising from the same protein are grouped to evaluate the peptide fold change dispersion. Protein-level inferences are performed utilizing all of the available peptide abundances and a likelihood ratio test to compute p-values (Karpievitch, et al., 2009a). Significant up or down protein expression changes are sorted and plotted by p-value from hypothesis testing through the sample types and the replicate analyses.

Results: Differential Proteomic Analysis of Control and LIRKO Hepatocyte Conditioned Media (HCM)

Hepatocytes from control and LIRKO mice were cultured in serum free medium and supernatants collected after 18 hrs.

To concentrate secreted proteins from diluted HCM and eliminate small molecules artefacts from the culture medium that do not allow LC-MS analysis, we developed a proteomic approach based on enrichment of the proteins using zeolite LTL nanocrystals as described by Cao J., et al. (Nanozeolite-driven approach for enrichment of secretory proteins in human hepatocellular carcinoma cells, Proteomics. 2009, 9, (21):4881-8) followed by enzymatic digestion of the proteins directly on nanobeads.

Figure 15:
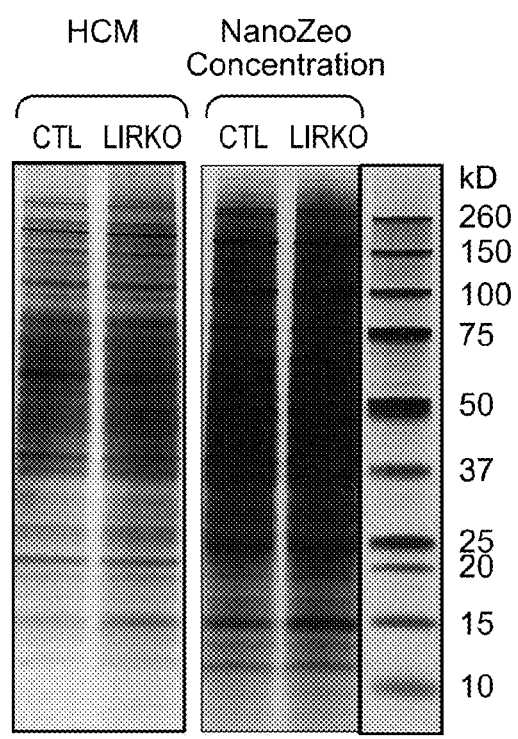
FIG. 15 shows an SDS/PAGE analysis of hepatocyte conditioned media from control and LIRKO mice before concentration(HCM) or after concentration of Nanozeolites. Proteins were detected by silver staining. Molecular weights are shown the right.

Before enzymatic digestion, adsorption of the proteins was controlled by SDS/PAGE (FIG. 15). Both LIRKO and control supernatants showed similar and highly complex protein profiles before and after adsorption onto nanoparticles.

The resulting peptides were identified using high-performance liquid chromatography tandem mass spectrometry LC-MS/MS analysis. Proteins were identified by searching MS and MS/MS data of peptides against the UniProtKB/Swiss-Prot protein knowledgebase using the MASCOT search engine and then quantified by a label free quantitative LC-MS analysis using in-house DIFFTAL software algorithm. Relative quantification of each protein was obtained by averaging the intensity ratios of the three most intense derived peptides (or two derived peptides if only two unique peptides were identified) as described in the experimental procedure.

We realized 3 independent proteomic analyses to compare LIRKO and control HCM starting from independent hepatocyte cultures from different mice.

We identified 514, 1670 and 1280 proteins in these 3 different analysis according to the concentration and amount of proteins available.

Among these proteins, we identified 12 proteins that were up-regulated and 8 proteins that were down-regulated in the LIRKO HCM with the respective ratio above 2 or under 0.5 and p-values lower than 0.05, in all the experiments.

Mouse SerpinB1 was identified by LC-MSMS by 12 unique tryptic peptides given a protein coverage of 37% and in the 3 independent experiments, SerpinB1 was shown to be up-regulated in LIRKO hepatocyte supernatants with the respective ratio of 17.5, 11.6 and 18.4 and p-values smaller than 0.01 (FIGS. 16A & B).

This up-regulation of SerpinB1 in LIRKO hepatocytes was confirmed at the RNA level by transcriptomic analysis of mouse liver explants showing that the differential observed at the protein level is due to an overexpression of the protein and not a modification of a secretory pathway in LIRKO mouse liver.

Transcriptomics Analysis of Liver Samples from LIRKO Model

Based on the above results, we next analyzed LIRKO mouse liver gene expression.

Animals and Sample Preparation:

The total number of mice used for gene expression analyses was 20 animals (3 months old [n=12 animals], and 24 months old [n=8 animals]). Liver tissue samples were excised rapidly from animals and snap-frozen in liquid nitrogen and stored at −80 degree Celsius (° C.).

Affymetrix GeneChip Analysis:

The general use of oligonucleotides arrays for gene expression monitoring has been described in U.S. Pat. No. 6,177,248. In our practical application, the used micro arrays (GeneChips) from Affymetrix, Santa Clara, Calif. USA contain deoxynucleotide sequences that represent approximately 39,000 mouse transcripts and variants from >34,000 well characterized mouse genes (Mouse Genome 430 2.0 GeneChip). Each transcript and variant is represented by 11 different oligonucleotide probes with 25 basepairs in length. Sequences used in the design of the array were selected from Gen Bank, dbEST, and RefSeq. The sequence clusters were created from the UniGene database (Build 107, June 2002) and then refined by analysis and comparison with the publicly available draft assembly of the mouse genome from the Whitehead Institute Center for Genome Research (MGSC, April 2002).

150 mg liver tissue were lysed in Qiagen RLT buffer with an UtraTurrax homogenizer. Total RNA from the tissue lysates was isolated with Qiagen RNeasy kit including proteinase K digestion, DNase digestion and an additional RNeasy cleanup step as recommended by the manufacturer (Qiagen). Integrity of RNA samples has been checked by RNA nano assay (Agilent 2100 BioAnalyzer).

First and second strand cDNA synthesis were performed with 10 μg of each total RNA using SuperScript SSI I RT polymerase system (lnvitrogen) and a T7(dT)24 primer (SEQ ID NO: 4) linking the T7 RNA polymerase promoter and oligo(deoxythymidine)24. Double strand cDNA was phenol-chloroform extracted followed by ethanol precipitation and resuspended in 12μl RNAse-free water. Biotin-UPT and -CTP labelled cRNA was transcribed in vitro using Enzo BioArray High Yield RNA Transcript Labelling Kit (Enzo Diagnostics) and purified by RNeasy cleanup and ethanol precipitation. Aliquots of every total RNA and cRNA were monitored before and after each purification step by UV-spectrophotometry, agarose gel electrophoresis and RNA nano assay (Agilent 2100 BioAnalyzer). 15 μg cRNA samples were fragmented at 94 degree Celsius for 35 min in 40 mM Tris/acetate pH 8.1, 100 mM KOAc and 30 mM MgOAc, added to hybridisation buffer and hybridised to Affymetrix GeneChip for 16-18 hours at 45 degree Celsius and 60 rpm in a rotating hybridization oven (Hybridization Oven 640, Affymetrix). Micro arrays were washed in a fluidics station (GeneChip Fluidics Station 450, Affymetrix) and double-stained with streptavidinphycoerythrin conjugate (Molecular Probes), anti-streptavidin antibody and again streptavidin-phycoerythrin conjugate to enhance signal intensity according to the methodologies described by Affymetrix. After washing the micro arrays were scanned with the GeneChip Scanner 3000 7G (Affymetrix), which is controlled by Affymetrix software GeneChip Operating System (GCOS) v1.4. Quality control of each chip was performed according the Affymetrix quality criteria, including mean average difference, raw intensity and 3'/5' ratio of housekeeping genes beta-actin and GAPDH.

Data Analysis

Figure 17:
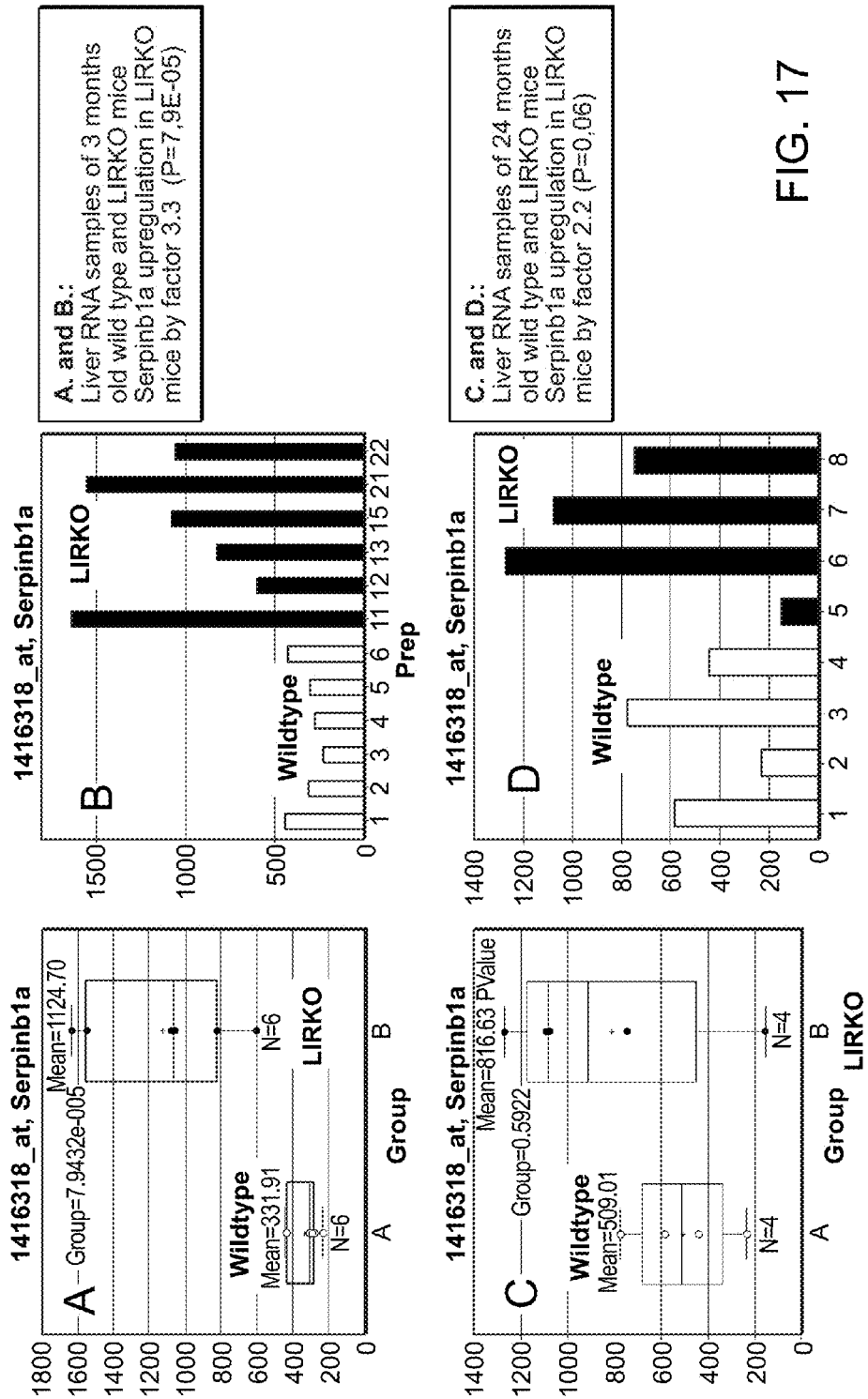
FIG. 17(A-D) shows SerpinB1(a) gene expression box plot (A & C) and bar chart (B & D) intensity data for Affymetrix probe set 1416318_at specific for SerpinB1(a) in liver samples from LIRKO and wildtype mice at 3 months (A & B) and at 24 months (C & D).

Bioinformatics analysis of the Affymetrix raw data has been performed in the Array Studio software package from OmicSoft Corp. Cary, N.C., USA. For this Affymetrix cell files have been first processed with Robust Multi-array Average (RMA) as normalization method and the data have been then log2 transformed. For detection of expressed genes all Affymetrix probe sets with intensity signals of <6 in at least 25% of the samples each of the LIRKO and wildtype group have been filtered out. Principal component analysis (PCA) has been applied to all samples as a quality control measure. To detect differentially expressed genes a pairwise ANOVA statistical test has been applied between the LIRKO and the wildtype control group. Criteria for determining differentially expressed genes with statistical significance were changes in expression levels higher than 2-fold and a P-value<0.05. The analysis result for Serpinb1a expression from Affymetrix probe set 1416318_at specific for Serpinb1a is shown in FIG. 1. Serpinb1a gene expression was found to be significantly up-regulated in liver samples from 3 months old LIRKO mice by a factor of 3.3. Significant up-regulation of Serpinb1 in liver could be confirmed in samples of 24 months old LIRKO. See FIG. 17.

Confirmation of Affymetrix and Proteomics Data

To confirm our Affymetrix and Proteomics data, we examined the expression of SerpinB1 in the liver and evaluated circulating levels of SerpinB1 in the LIRKO mouse. We observed that SerpinB1 mRNA (LIRKO 2.4±0.6 vs. control 0.6±0.1, p<0.05, n=6) and protein levels (LIRKO 5.1±0.9 vs. control 1.1±0.06, p<0.05, n=4-5) are 5-fold higher in 3-month-old LIRKO mice compared to age-matched controls. Moreover, circulating SerpinB1 was increased in sera of both 3-month-old (LIRKO 7.9±1.4 vs. control 3.6±0.3, p<0.05, n=5-6) and 12-month-old (LIRKO 10.6±0.9 vs. control 7.7±0.5, p<0.05, n=4-5) LIRKO mice.

Similar data were obtained when SerpinB1 was assayed in plasma (data not shown). We next evaluated the expression level of SerpinB1 in livers harvested from other models of insulin resistance: leptin-deficient (ob/ob) mice and high fat diet (HFD) mice. Similar to LIRKO mice, we demonstrated that mRNA (ob/ob 4.9±1.5 vs. control 1.3±0.2, p=0.07, n=5) and protein (ob/ob 3.4±0.5 vs. control 1.3±0.2, p<0.05, n=5) expression of liver SerpinB1 is upregulated in ob/ob mice. Further, SerpinB1 protein abundance was 2-fold higher (HFD 3.2±0.3 vs. control 1.6±0.3, p<0.01, n=6) in livers derived from HFD compared to control animals. Together, these data strongly implicate SerpinB1 as a potential "biomarker" of insulin resistance.

Example 7

Effects of SerpinB1 and Neutrophil Elastase Inhibitors on β-Cell Proliferation

Figure 12:
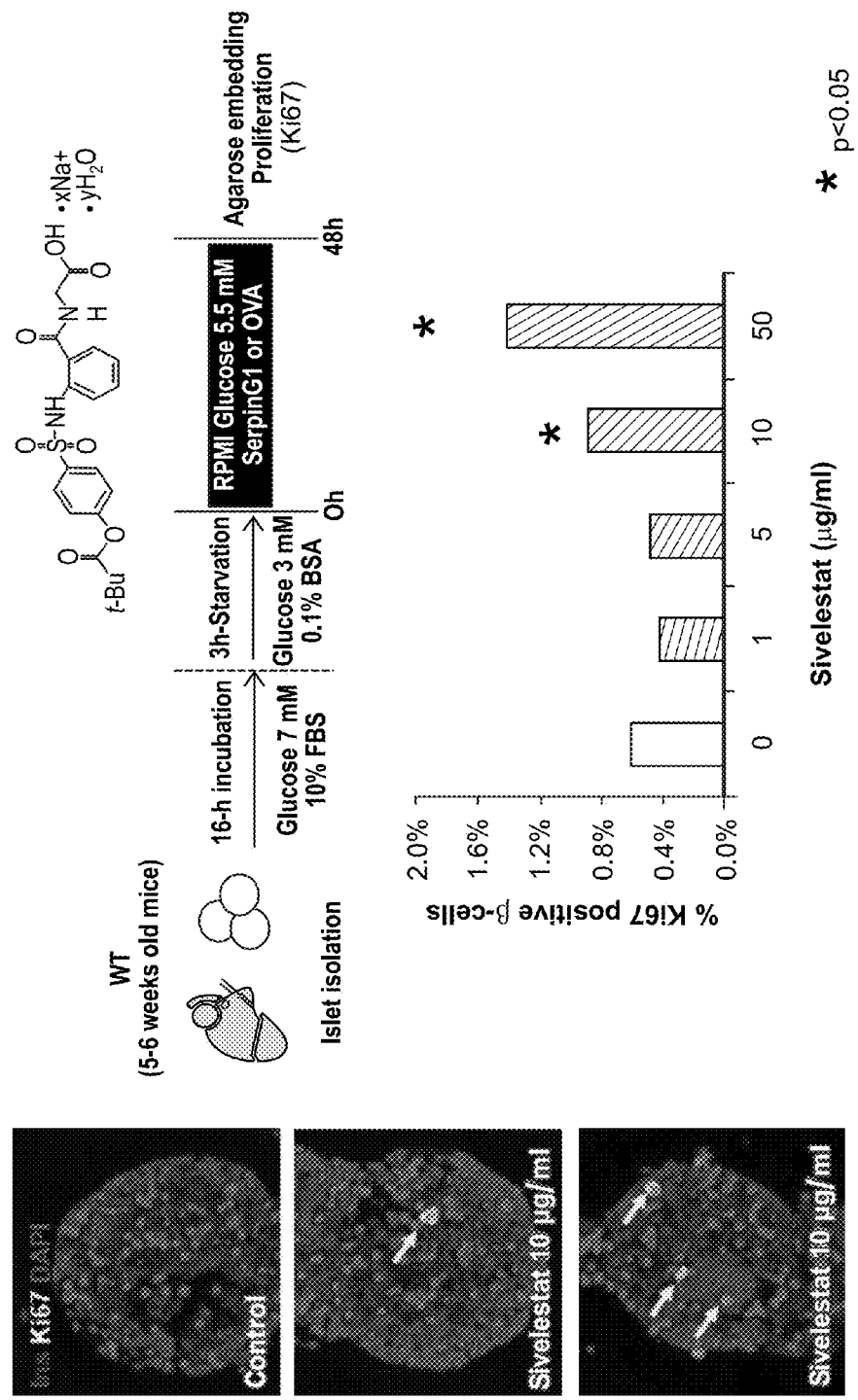
FIG. 12 shows the stimulation of islet β cell replication in vitro.

To test whether SerpinB1 is a β-cell growth factor, we cultured freshly isolated primary mouse islets in presence of various doses of recombinant human SerpinB1 or ovalbumin (SerpinB14) and evaluated β-cell proliferation by Ki67 immunofluorescent staining (known to those of ordinary skill in the art). We observed that while mouse islets cultured in ovalbumin (1 µg/ml) displayed normal low β-cell proliferation, isolated islets cultured with recombinant SerpinB1 exhibited a dose-dependent increase in Ki67+ insulin+ cells; the data reached statistical significance when islets were cultured at a concentration of 1 µg/ml of SerpinB1 compared to controls (islets cultured at a similar concentration of ovalbumin). A major substrate of SerpinB1 is neutrophil elastase. To investigate whether the proliferative action of SerpinB1 is mediated by antagonizing neutrophil elastase activity, we assessed the ability of the neutrophil elastase inhibitor, Sivelestat (Sivelestat is the International Nonproprietary Name (INN) as given by the World Health Organization (WHO); the chemical name is: N-{2-[({4-[(2,2-dimethylpropanoyl)oxy]phenyl}sulfonyl)amino]benzoyl}glycine), to stimulate islet β-cell proliferation in vitro. Using various doses, we observed that low doses (1 and 5 µg/ml; see FIG. 12) do not enhance β-cell proliferation. Conversely, a substantial increase in the number of proliferating insulin+ cells was observed in islets cultured at higher doses (e.g. 10 and 50 µg/ml). Importantly, Sivelestat at a dose of 100 µg/ml increased the number of human (EndoC-βH1) Ki67 positive β-cells compared to non-treated cells.

Example 8

Effect of SerpinB1 on Proliferation of Mouse and Human β-Cell In Vitro and In Vivo To directly assess the role of SerpinB1 on β-cell replication in vitro, mouse hepatocytes will be infected with constructions overexpressing SerpinB1 or negative constructions for 24, 48 or 96 hours. One of ordinary skill in the art is capable of constructing suitable expression vectors. Cultured media from infected cells will be used to stimulate mouse or human primary islets and β-cell proliferation will be assessed in in vitro assays. To assess the impact of SerpinB1 on β-cell proliferation in vivo we are generating Associated-adenoviruses (AAV) driving the expression of SerpinB1a (using, for example, the sequences of FIGS. 13 and 14) using a ubiquitous CMV promoter or a liver specific promoter albumin promoter. Injection of AAV-albumin-SerpinB1 via the tail injection will allow for over-expression of the SerpinB1 in the liver. The effects of this over-expression on β-cell proliferation will be assessed 12-16 weeks after injection of the AAV.

In a second model, mice over-expressing the AAV-SerpinB1 in the liver will be transplanted with human islets to create a "humanized mouse model". Mice will be monitored for body weight, blood glucose for 2, 4 and 16 weeks. At the end of the experiment, islet grafts and pancreases will be harvested and analyzed for proliferation and survival of endocrine cells. This model will directly indicate whether altering the expression of SerpinB1 in the liver promotes human β-cell proliferation in vivo—with important implications for human therapy.

Example 9

Mechanisms Underlying the Actions of SerpinB1

To gain insights into the mechanisms underlying the effects of SerpinB1 we will undertake several approaches as outlined below:

a) Examine how expression of SerpinB1 using an adeno-associated-virus (AAV-SerpinB1) in the liver will potentially impact β-cell proliferation. The AAV-SerpinB1 reagent is currently being produced.

b) Plasma membrane localization of SerpinB1 substrates in hepatocytes and pancreatic β-cells. We will first analyze the localization of SerpinB1 by immunostaining and western blotting of hepatocytes and β-cells to investigate whether the major substrate of SerpinB1 (neutrophil elastase) is expressed at the plasma membrane. We will also analyze expression and localization of other substrates including proteinase 3 and chymase.

c) Identification of signaling cascades downstream of SerpinB1. Mouse and human islets treated with SerpinB1 and Sivelestat for 5, 10, and 60 minutes will be subjected to proteomics analysis to identify substantial variations in key phospho-protein signaling molecules.

d) We will dissect the SerpinB1 signaling pathway(s) by creating gain-of function and loss-of function mouse models of potential candidates identified in b).

e) The role of SerinB1 as permissive factor insulin signaling: We will examine how SerpinB1 interacts with proteins in other growth factors (e.g. insulin and insulin-like-growth factor1) to investigate whether the effects are additive or synergistic.

f) A recent study showed that mice injected with recombinant neutrophil elastase demonstrated decreased levels of IRS-1 and downstream signaling in liver (Saswata, et al, *Nature Medicine* 2012). Therefore, one plausible mechanism by which SerpinB1 and Sivelestat are acting may be directly related to their ability to limit the Neutrophil elastase-mediated IRS-1 down-regulation. In this context, we plan to analyze whether SerpinB1 act as factor enhancing the expression and activation of elements of insulin signaling including IRS-1 and downstream signaling molecules.

g) We plan to undertake studies in human islets and human β-cells to further establish the role of SerpinB1 and related family members on their ability to safely and significantly enhance β-cell proliferation with the long term goal of using this approach to enhance functional β-cell mass in humans with diabetes.

All studies discussed above have therapeutic implications.

5) Anticipated Results: We describe the identification of a new liver-derived β-cell growth factor promoting β cell proliferation in the context of insulin resistance. Preliminary data demonstrate that "SerpinB1" is crucial to promote β-cell mass. The studies in progress and planned will provide additional data to support the potential use of SerpinB1 and/or the modulation of SeprinB1 production and function, and one or more of its family members (e.g., Glade B family), as potential therapeutic agents to enhance functional β-cell mass in humans for the treatment and/or prevention of type 1 and type 2 diabetes in humans.

Experimental Procedures—not Noted Elsewhere Herein

Animals

Mice were housed in pathogen-free facilities and maintained on a 12 hr light/dark cycle in the Animal Care Facility at Joslin Diabetes Center, Boston, and the Foster Biomedical Research Laboratory, Brandeis University, Waltham, Mass. All studies conducted and protocols used were approved by the Institutional Animal Care and Use Committee of the Joslin Diabetes Center and Brandeis University and were in accordance with NIH guidelines. LIRKO mice were generated by crossing Albumin-Cre to IR$^{flox/flox}$ on a mixed genetic background and were backcrossed for more than 15 generations on the C57/Bl6 background. LIRKO mice (Albumin-Cre$^{+/-}$·IR$^{flox/flox}$) and their littermate Lox controls (Albumin-Cre$^{-/-}$·IR$^{flox/flox}$) were genotyped as described previously by Okada et al. (2007, Insulin receptors in beta-cells are critical for islet compensatory growth response to insulin resistance. Proc. Natl. Acad. Sci. USA 104, 8977-8982). Blood glucose was monitored with an automated glucose monitor (Glucometer Elite; Bayer), and plasma insulin was detected by ELISA (Crystal Chem).

Parabiosis

Parabiosis surgery was performed as described earlier by Eggan et al. (2006, Ovulated oocytes in adult mice derive from non-circulating germ cells. Nature 441, 1109-1114). Cross-circulation was determined 2 weeks after surgery by Evans Blue transmission (Pietramaggiori, G., et al., (2009). Improved cutaneous healing in diabetic mice exposed to healthy peripheral circulation. J. Invest. Dermatol. 129, 2265-2274). Body weight and blood glucose of parabiont animals were monitored weekly. After a 16 week parabiosis period, animals were sacrificed, and pancreases were collected for morphometric analysis.

Islet Isolation and Transplantation

Islets were isolated from 9-month-old mice using the intraductal collagenase technique (Kulkarni, R. N., et al., (1999). Altered function of insulin receptor substrate-1-deficient mouse islets and cultured beta-cell lines. J. Clin. Invest. 104, R69-R75). Islets were handpicked, concentrated in a pellet, and kept on ice until transplantation (Flier, S. N., at al., (2001). Evidence for a circulating islet cell growth factor in insulin-resistant states. Proc. Natl. Acad. Sci. USA 98, 7475-7480). Surgery was performed in mice after intraperitoneal injection (15 ml/g body weight) of a 1:1 (w/v) mixture of 2,2,2-tribromoethanol and tert-amyl alcohol and diluted 1:50 with PBS (pH 7.4). The capsules of the kidneys were incised, and the islets were implanted near the upper pole of each kidney in 5-month-old male mice. The capsules were cauterized, and the mice were allowed to recover on a heating pad.

Growth Factors and Hormones Assays

ELISA-based assays were used to measure growth factors and hormones, including IGF-1 (catalog #MG100; R&D Systems), HGF (catalog #ab100686; Abcam), EGF (catalog #IB39411; IBL-America), PDGFAA (catalog #DAA00B; R&D Systems), PDGFBB (catalog #MBB00; R&D Systems), VEGF (Millipore), FGF21 (catalog #EZRMFGF21-26K; Millipore), Gastrin (catalog #E91224mu; USCN Life Science), Adiponectin (catalog #EZMADP-60K; Millipore), Ostepontin (catalog #MOST00; R&D Systems), and Osteocalcin (catalog #EIA4010; International). Multiplex-based assays were used to measure endocrine hormones (catalog #MENDO-75; Millipore), gut hormones (catalog #MGT-78K; Millipore), adipokines (catalog #MADPK-71 K; Millipore), and Cytokines/Chemokines (catalog #MPXM-CYTO-70K.Ixt; Millipore).

Serum Stimulation

Sera were obtained after coagulated blood was centrifuged twice for 15 min at 8,000 rpm at 4° C. and stored at ~80° C. until use. Pancreatic islets were isolated from 5-week-old male mice by liberase and thermolysin digestion (Roche), handpicked, and cultured for 16 hr in RPMI 1640 with 7 mM glucose and 10% FBS (v/v). A total of 150 size-matched mouse islets were starved in RPMI 1640 with 0.1% BSA (v/v) containing 3 mM glucose for 3 hr and thereafter treated with RPMI 1640 with 5.5 mM glucose supplemented every 12 hr with 10% (v/v) serum obtained from 3- or 12-month-old LIRKO and control mice. Twenty-four to 48 hr later, islets were handpicked, fixed with 4% paraformaldehyde, embedded in agarose/paraffin, and sectioned for immunohistochemistry studies. To evaluate β cell replication, sections were analyzed by fluorescent microscopy subsequent to Ki67, TUNEL, and insulin immunostaining.

LECM Stimulation

Liver explant-conditioned medium (LECM) preparation was adapted from Nicoleau et al. (2009, Endogenous hepatocyte growth factor is a niche signal for subventricular zone neural stem cell amplification and self-renewal. Stem Cells 27, 408-419). Mice were anesthetized with Avertin (240 mg/kg intraperitoneally), and 100 mg liver explants were dissected from LIRKO or control mice. Explants were washed twice in cold PBS, incubated in PBS at 37° C. for 30 min, and then cultured in serum-free Dulbecco's modified Eagle's medium (DMEM) containing 5.5 mM glucose. After a 3 day incubation, LECM were collected, centrifuged, and kept at ~80° C. till use. Islets were initially starved for 3 hr in DMEM containing 3 mM glucose and 0.1% BSA and thereafter stimulated for 24 hr with DMEM/5.5 mM glucose media containing 10% LECM. Islet β cell proliferation and apoptosis were analyzed by fluorescent microscopy after Ki67, TUNEL, and insulin immunostaining.

HCM Stimulation

Hepatocytes were isolated from 6-month-old LIRKO and control mice by collagenase digestion via portal vein perfusion (Sun, R., et al., (2005). IL-6 modulates hepatocyte proliferation via induction of HGF/p21 cip1: regulation by SOCS3. Biochem. Biophys. Res. Commun. 338, 1943-1949). Mice were anesthetized with Avertin (240 mg/kg intraperitoneally), and the portal vein was cannulated with JELCO 22G×1 inch catheter (Smiths Medical). The liver was perfused with EGTA solution (5.4 mmol/l KCl, 0.44 mmol/l KH$_2$PO$_4$, 140 mmol/l NaCl, 0.34 mmol/l Na$_2$HPO$_4$, and 0.5 mmol/l EGTA [pH 7.4]) and digested with DMEM containing 0.075% type I collagenase. Hepatocytes were washed twice in Hepatocyte Wash Medium (Invitrogen). The isolated mouse hepatocytes were seeded in collagen-coated 6-well plates (BD BioCoat) at a density of 106 cells/well in DMEM containing 25 mM glucose and 10% FBS (v/v). Sixteen hours later, hepatocytes were cultured for 24 hr in serum-free DMEM containing 5.5 mM glucose. HCM was collected, centrifuged, and kept at ~80° C. Islets were initially starved for 3 hr in DMEM containing 3 mM glucose and 0.1% BSA and thereafter incubated for 24 hr in DMEM/5.5 mMglucose media containing 50% HCM. Islet β cell proliferation and apoptosis were analyzed by fluorescent microscopy after Ki67, TUNEL, and insulin immunostaining.

Human Islet Studies

Human islets were obtained from the Integrated Islet Distribution Program. All studies and protocols used were approved by the Joslin Diabetes Center's Committee on Human Studies (CHS#5-05). Upon arrival, islets were cultured overnight in Miami Media #1A (Cellgro). The islets were then starved in Final Wash/Culture Media (Cellgro) for 3 hr prior to stimulation with serum (diluted to 10% v/v), LECM (diluted to 10% v/v), or HCM (diluted to 50% v/v) for 24 hr.

Immunostaining Studies

Pancreases and islets were analyzed by immunostaining using anti-Ki67 (BD), anti-insulin (Abcam), or anti-glucagon (Sigma-Aldrich) antibodies.

Counting Proliferating β Cells

In all experiments, cell counting was manually performed in a blinded fashion by a single observer. BrdU+ or Ki67+β cells were assessed by immunofluorescence microscopy. Insulin+ cells showing nuclear DAPI staining were considered as β cells. Insulin+ cells showing nuclear colocalized staining for DAPI+ and Ki67+ (or BrdU+) were counted as proliferating β cells. The double-positive cells (Ins+/BrdU+ or Ins+/Ki67+) were confirmed in randomly selected cells in all experiments by confocal microscopy.

BrdU Injection Studies

Mice were injected with BrdU intraperitoneally (100 mg/kg body weight) 5 hr prior to animal sacrifice for immunostaining of the pancreas. BrdU injections in the in vivo serum administration experiments were performed on three occasions as denoted in FIG. 2A.

Statistical Analysis

All data are presented as mean±SEM and analyzed using unpaired, two-tailed Student's t test. A p value of less than 0.05 is considered significant.

---

What is claimed is:

1. A method of promoting pancreatic β cell proliferation in vitro, said method comprising:

contacting a population of human pancreatic β cells with an isolated SerpinB1 protein thereby promoting pancreatic β cell proliferation.

2. A method of promoting pancreatic β cell proliferation in vivo comprising administering a SerpinB1 protein in a pharmacological carrier to a subject in need thereof, thereby promoting pancreatic β cell proliferation in the subject.

3. The method of claim 2, wherein the subject has impaired glucose tolerance.

4. The method of claim 3, wherein administering said SerpinB1 protein to said subject with impaired glucose tolerance improves glycemic control or improves insulin sensitivity.

5. The method of claim 2, wherein the subject is at risk of developing diabetes.

6. The method of claim 2, wherein the subject suffers from type 1 or type 2 diabetes.

7. The method of claim 2, further comprising detecting glycemic control in the subject, wherein an increase in glycemic control indicates pancreatic β cell proliferation in vivo.

* * * * *

SEQUENCE LISTING

<160> NUMBER OF SEQ ID NOS: 4

<210> SEQ ID NO 1
<211> LENGTH: 1931
<212> TYPE: DNA
<213> ORGANISM: Mus musculus

<400> SEQUENCE: 1

```
acttcatcct agctgtaagt ggagccagac ctgctaagca agagacttca ccatggagca      60
gctgagttca gccaacaccc tcttcgcctt ggagctgttc caaaccctga atgaaagcag     120
ccccacagga aacatcttct tctctccctt cagcatttct tctgccttgg ccatggtcat     180
tctgggggcc aaaggcagca ctgcagctca gctttctaag acttttcatt ttgactctgt     240
tgaggacatc cattcacgct tccaaagcct gaatgctgaa gtgagcaaac gtggagcatc     300
tcacactctg aaacttgcta acagactgta tggagagaaa acctacaact tccttcctga     360
atacttggct tcaacccaga aaatgtatgg tgctgacttg gcccctgtgg attttctgca     420
tgcctctgag gatgcaagga aggagataaa ccagtgggtc aaaggtcaaa cagaagggaa     480
aatcccagaa ctgttgtctg tgggtgtggt ggacagtatg accaaacttg tgctggtgaa     540
tgccatctac tttaagggaa tgtgggagga gaaattcatg acagaggaca caacggatgc     600
tccattccga ctgagtaaga aagacacaaa aacagtgaag atgatgtatc aaaagaaaaa     660
atttccattt ggttacattt cggacctgaa gtgcaaggtg ctggagatgc cttaccaggg     720
tggagaactt agcatggtca ttctgctgcc taaagacatt gaggacgagt ccacgggtct     780
taagaagatt gaaaagcaaa taactttgga aaaactgctt gaatggacca aacgtgagaa     840
cttggaattc attgatgtcc acgtcaaact gccccggttc aagatagaag agagctatac     900
cctcaactct aacctgggcc gcctgggagt gcaggatctc tttagcagta gcaaggctga     960
tctctctggc atgtcaggat ccagagatct tttcatatca aaaattgtcc acaagtcctt    1020
tgtggaagtg aatgaggaag gaacagaggc agccgctgct acaggaggca ttgctacatt    1080
ctgtatgttg ttgcctgagg aagaattcac agtggaccat ccgttcattt tcttcattcg    1140
gcacaatccc acatctaatg tgctcttcct tggcagggtt tgttccccat agaagaagga    1200
gactttacag atacaaggca gagcttagag tttcattccc tgagatttta atagtgatta    1260
ttttcatttg tacttgacaa taaaaactct aaccagaaac caatctttct tttgtatgtt    1320
caaccctgtt agctctttat atccatgact tttggcatgg gtatgtctat tttgattgta    1380
caatgaaagc aggactcctg ttttcctcct cggcttttgc atgacctcca gagtacatca    1440
```

-continued

| | |
|---|---|
| aaggttcata gctaggctga aaattctgga cgactccatc ctcaaacttt atggactgta | 1500 |
| ggtgggtgcc tgcagatgct aactgaagtc atatccatct ggggtagcgt ggatacccott | 1560 |
| aagcctcaaa tcattattac aatctgcttt tcaagtacaa catccagagt ataatcaaag | 1620 |
| ataactgttt gggtgggcag ccatggcaac agagatacaa agcagcacaa acaaaagaga | 1680 |
| aggacaacag tggaaggctc taaatgctgc tgccgcccat acaaaccaga gaacaacagt | 1740 |
| ctgtgaagat aatattgacg aaatccaagg tcagatactt tagcaggcta ttgcaaactt | 1800 |
| acaaacaaca tttcatgtct ggatgaaaag gaactagaaa ccccagagct taaacataca | 1860 |
| ataaattatt tccattgaaa acttaaataa taaagaattt gtggattttt aagtctgaaa | 1920 |
| aaaaaaaaaa a | 1931 |

<210> SEQ ID NO 2
<211> LENGTH: 2678
<212> TYPE: DNA
<213> ORGANISM: Homo sapiens

<400> SEQUENCE: 2

| | |
|---|---|
| agaaagaagc cgcgcccctg aggagggcgc tgcccggaag ccacgctcac ttctgcttgc | 60 |
| acttaggcga cctcgggagc tcggactcct acgcagtcac cgggaagggc cgccgccccg | 120 |
| cccgcggctg ctggcccggg tgacgcttcc gcctgctata agagcagcgg ccctcggtgc | 180 |
| ctccttcctg acctcgcacc cagctcggag cccggagcgt gcctcggcgg cctgtcggtt | 240 |
| ttcaccatgg agcagctgag ctcagcaaac acccgcttcg ccttggacct gttcctggcg | 300 |
| ttgagtgaga acaatccggc tggaaacatc ttcatctctc ccttcagcat ttcatctgct | 360 |
| atggccatgg ttttctgggg accagaggt aacacggcag cacagctgtc caagactttc | 420 |
| catttcaaca cggttgaaga ggttcattca agattccaga gtctgaatgc tgatatcaac | 480 |
| aaacgtggag cgtcttatat tctgaaactt gctaatagat tatatggaga gaaaacttac | 540 |
| aatttccttc ctgagttctt ggtttcgact cagaaaacat atggtgctga cctggccagt | 600 |
| gtggattttc agcatgcctc tgaagatgca aggaagacca taaaccagtg ggtcaaagga | 660 |
| cagacagaag gaaaaattcc ggaactgttg gcttcgggca tggttgataa catgaccaaa | 720 |
| cttgtgctag taaatgccat ctatttcaag ggaaactgga aggataaatt catgaaagaa | 780 |
| gccacgacga atgcaccatt cagattgaat aagaaagaca gaaaaactgt gaaaatgatg | 840 |
| tatcagaaga aaaaatttgc atatggctac atcgaggacc ttaagtgccg tgtgctggaa | 900 |
| ctgcccttacc aaggcgagga gctcagcatg gtcatcctgc tgccggatga cattgaggac | 960 |
| gagtccacgg gcctgaagaa gattgaggaa cagttgactt tggaaaagtt gcatgagtgg | 1020 |
| actaaacctg agaatctcga tttcattgaa gttaatgtca gcttgcccag gttcaaactg | 1080 |
| gaagagagtt acactctcaa ctccgacctc gcccgcctag tgtgtcagga tctctttaac | 1140 |
| agtagcaagg ctgatctgtc tggcatgtca ggagccagag atatttttat atcaaaaatt | 1200 |
| gtccacaagt catttgtgga agtgaatgaa gagggaacag aggcggcagc tgccacagca | 1260 |
| ggcatcgcaa ctttctgcat gttgatgccc gaagaaaatt tcactgccga ccatccattc | 1320 |
| cttttctttta ttcggcataa ttcctcaggt agcatcctat tcttggggag attttcttcc | 1380 |
| ccttagaaga aagagactgt agcaatacaa aaatcaagct tagtgcttta ttacctgagt | 1440 |
| ttttaataga gccaatatgt cttatatctt taccaataaa accactgttc agaaacaagt | 1500 |
| cttttcattttt ctttgtaagt ttggctctgt tggctgttta cacccatgaa ttttggcatg | 1560 |

```
ggtatctatt tttctttttt acattgaaaa aaatccagtg gttgcttttg aatgcatcaa    1620
gtaaagaaga agaaaagaat acatccgatg cgtagattct tgaccatgta gtaatctata    1680
aaattgctat atcctcctga tagccatggg aaaacatgat aagatggtca tttatttgc    1740 agttagaatt ttggaagcca caaaatagac agacaccctg actgttgaag ggaggtttaa    1800
aaacagatat tcaattgaaa tgtaagagag cacccccaatt gagagcccag gttacgaaga    1860
caagcttgcc tcgcctgact tttctgtccc ttgttctgca ggattagtat tctgttacag    1920
acctctagtt tttagactct tcaattaaag ggccaatggt tataacctgc attccctttt    1980
ttgttcttct ttatgtataa tatatagttc atgtggcgct gcatgaaatc aagaagtggg    2040
tgtcttagga taaagatac caagagtcta caaaaataac catgtagtaa gataaactgc    2100
tgaacaaagg ttttactgtt agccaccttc tcatgtgttt tcttttctct ttttcttttt    2160
ctttctttct ttctttttttt ttttttttgag acagagtctt gctctgttac ccaggctgga    2220
gtgcagtggc acgatctcag ctcaccgcaa cctctgcctc ctgggttcaa gtgattctct    2280
tgcttcagcc tcctgagtag ctgggattat aggcatgcac cactaggcct ggctaattt    2340 tgtatttta gtagagatgg ggttttccaa tgttggccag ctggtcccg aactcctgac    2400 ctcaggtgat ccgcgcacct cagcctccca aagtgctggg attacaggca tgagctacca    2460
tgcctggcct tctcatgtgt tttctgatta aggctcttga cttccaaggc tgtgtggga    2520 gatgggtgg gggctcttgg actgatataa aactttgtca aatgtagttc tttgaatgga    2580
gcttgaaacg ccgcatattc ttgctcccac aaggatagtg ggcatcatga attaataaaa    2640
cgtcctagga ttctgcaagc taaaaaaaaa aaaaaaaa                             2678
```

```
<210> SEQ ID NO 3
<211> LENGTH: 379
<212> TYPE: PRT
<213> ORGANISM: Mus musculus

<400> SEQUENCE: 3

Met Glu Gln Leu Ser Ser Ala Asn Thr Leu Phe Ala Leu Glu Leu Phe
1               5                   10                  15

Gln Thr Leu Asn Glu Ser Ser Pro Thr Gly Asn Ile Phe Phe Ser Pro
            20                  25                  30

Phe Ser Ile Ser Ser Ala Leu Ala Met Val Ile Leu Gly Ala Lys Gly
        35                  40                  45

Ser Thr Ala Ala Gln Leu Ser Lys Thr Phe His Phe Asp Ser Val Glu
    50                  55                  60

Asp Ile His Ser Arg Phe Gln Ser Leu Asn Ala Glu Val Ser Lys Arg
65                  70                  75                  80

Gly Ala Ser His Thr Leu Lys Leu Ala Asn Arg Leu Tyr Gly Glu Lys
                85                  90                  95

Thr Tyr Asn Phe Leu Pro Glu Tyr Leu Ala Ser Thr Gln Lys Met Tyr
            100                 105                 110

Gly Ala Asp Leu Ala Pro Val Asp Phe Leu His Ala Ser Glu Asp Ala
        115                 120                 125

Arg Lys Glu Ile Asn Gln Trp Val Lys Gly Gln Thr Glu Gly Lys Ile
    130                 135                 140

Pro Glu Leu Leu Ser Val Gly Val Val Asp Ser Met Thr Lys Leu Val
145                 150                 155                 160

Leu Val Asn Ala Ile Tyr Phe Lys Gly Met Trp Glu Glu Lys Phe Met
                165                 170                 175
```

-continued

```
Thr Glu Asp Thr Thr Asp Ala Pro Phe Arg Leu Ser Lys Lys Asp Thr
            180                 185                 190

Lys Thr Val Lys Met Met Tyr Gln Lys Lys Phe Pro Phe Gly Tyr
        195                 200                 205

Ile Ser Asp Leu Lys Cys Lys Val Leu Glu Met Pro Tyr Gln Gly Gly
        210                 215                 220

Glu Leu Ser Met Val Ile Leu Leu Pro Lys Asp Ile Glu Asp Glu Ser
225                 230                 235                 240

Thr Gly Leu Lys Lys Ile Glu Lys Gln Ile Thr Leu Glu Lys Leu Leu
                245                 250                 255

Glu Trp Thr Lys Arg Glu Asn Leu Glu Phe Ile Asp Val His Val Lys
                260                 265                 270

Leu Pro Arg Phe Lys Ile Glu Glu Ser Tyr Thr Leu Asn Ser Asn Leu
                275                 280                 285

Gly Arg Leu Gly Val Gln Asp Leu Phe Ser Ser Ser Lys Ala Asp Leu
        290                 295                 300

Ser Gly Met Ser Gly Ser Arg Asp Leu Phe Ile Ser Lys Ile Val His
305                 310                 315                 320

Lys Ser Phe Val Glu Val Asn Glu Glu Gly Thr Glu Ala Ala Ala Ala
                325                 330                 335

Thr Gly Gly Ile Ala Thr Phe Cys Met Leu Leu Pro Glu Glu Glu Phe
                340                 345                 350

Thr Val Asp His Pro Phe Ile Phe Phe Ile Arg His Asn Pro Thr Ser
                355                 360                 365

Asn Val Leu Phe Leu Gly Arg Val Cys Ser Pro
        370                 375

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tttttttttt tttttttttt tttt                                            24
```